United States Patent [19]

Stamler et al.

[11] Patent Number: 5,380,758

[45] Date of Patent: Jan. 10, 1995

[54] S-NITROSOTHIOLS AS SMOOTH MUSCLE RELAXANTS AND THERAPEUTIC USES THEREOF

[75] Inventors: Jonathan Stamler, Chapel Hill, N.C.; Joseph Loscalzo, Dover, Mass.; Adam Slivka, Randolph, Mass.; Daniel Simon, Waban, Mass.; Robert Brown, Natick, Mass.; Jeffrey Drazen, Winchester, Mass.

[73] Assignee: Brigham and Women's Hospital, Boston, Mass.

[21] Appl. No.: 943,834

[22] Filed: Sep. 14, 1992

Related U.S. Application Data

[63] Continuation-in-part of Ser. No. 804,665, Dec. 11, 1992, abandoned, which is a continuation-in-part of Ser. No. 676,691, Mar. 29, 1991, abandoned.

[51] Int. Cl.$^6$ .................... A61K 31/195; A61K 38/00
[52] U.S. Cl. .................................................... 514/562
[58] Field of Search ........................................ 514/562

[56] References Cited

U.S. PATENT DOCUMENTS

| | | | |
|---|---|---|---|
| 3,184,505 | 5/1965 | Martin et al. | 260/534 |
| 4,900,719 | 2/1990 | Means et al. | 514/18 |
| 5,002,964 | 3/1991 | Loscalzo | 514/423 |
| 5,025,001 | 6/1991 | Loscalzo et al. | 514/91 |
| 5,116,861 | 5/1992 | Goto et al. | 514/427 |

FOREIGN PATENT DOCUMENTS

WO 92/17445 10/1992 WIPO .

OTHER PUBLICATIONS

Furchgott, R., Endothelium–Dependent Relaxation in Systemic Arteries in Relaxing and Contracting Factors, Human Press, New Jersey, pp. 1–26 (1988).

Hata, F., et al., Dissociation of cyclic GMP level and nitric oxide–induced inhibitory responses in rat colon, Japanese Journal of Pharmacology, 58 Suppl. 2:387P (1992). (Abstract only).

Robinson, Differences in response to dilator agents in blood vessels of different types: physiological bases for selectivity, Journal of Hypertension, 7:S147–S151 (1989).

Nakatsu K. et al., Role of cGMP in relaxation of vascular and other smooth muscle [Review], Canadian Journal of Physiology & pharmacology, 67(4):251–62 (Apr. 1989). (Abstract only).

Gaston et al., Endogenous nitrogen oxides and broncho–dilator S–nitrosothiols in human airways, Proc. Natl. Acad. Sci. USA, 90:10957–10961 (Dec. 1993).

Aldred et al., Kinetics and Mechanism of the Nitrosation of Alcohols, Carbohydrates, and a Thiol, *J.C.S. Perkin Trans. II* 777–782 (1982).

Buga et al., Endothelium–derived nitric oxide relaxes nonvascular smooth muscle, *Eur. J. Pharm.* 161:61–72 (1989).

(List continued on next page.)

*Primary Examiner*—Johann Richter
*Assistant Examiner*—Rebecca Look
*Attorney, Agent, or Firm*—Charles J. Herron; Elliot M. Olstein

[57] ABSTRACT

S-nitrosothiols exert a potent relaxant effect, mediated both by guanylate cyclase, and a cGMP-independent mechanism, upon non-vascular smooth muscle. Such types of smooth muscle include airway, gastrointestinal, bladder, uterine and corpus cavernosal. Thus, S-nitrosothiols may be used for the treatment or prevention of disorders associated with relaxation of smooth muscle, such as airway obstruction, and other respiratory disorders, bladder dysfunction, premature labor and impotence. Additionally, S-nitrosothiols may be used to alleviate smooth muscle contraction and spasm, and thus facilitate procedures involving diagnostic instrumentation, such as endoscopy, bronchoscopy, laparoscopy and cystoscopy. S-nitrosothiols also increase the binding affinity between hemoglobin and oxygen, and therefore, may be used to improve hemoglobin-oxygen binding, and oxygen transport to bodily tissues.

23 Claims, 21 Drawing Sheets

OTHER PUBLICATIONS

Byler et al., Spectroscopic Estimation of the Extent of S-Nitrosothiol Formation by Nitrite Action on Sulfhydryl Groups, *J. Agric. Food Chem.* 31:523–527 (1983).

Cocks et al., Comparison of relaxation responses of vascular and non-vascular smooth muscle to endothelium-derived relaxing factor (EDRF) . . . , *Naunyn-Schmiedeberg's Arch. Pharmacol.* 341:364–372 (1990).

Cooke et al., Flow stimulates endothelial cells to release a nitrovasodilator that is potentiated by reduced thiol, *Am J. Physiol.* 259(3):H804–H812 (1990).

Dusting et al., Endothelium-Derived Relaxing Factor Released From Cultured Cells: Differentiation From Nitric Oxide, *Clin. Exper. Pharm. Physiol.* 15:83–92 (1988).

Fung et al., Mechanisms for the Pharmacologic Interaction of Organic Nitrates with Thiols. Existence of and Extracellular Pathway for the Reversal of . . . , *J. Pharm. Exper. Ther.* 245(2):524–530 (1988).

Gaston et al., Relaxation of Human Airways In Vitro By S-Nitrosothiols, *Rev. Resp. Dis.* 145(4 pt. 2): A383 (1991).

Gaston et al., S-Nitrosothiols Are Stable Forms of NO That Relax Human Airways: Implications For Inflammatory and Immune Disease States, Abstract presented at Nitric Oxide Meeting Sep. 15, 1992.

Gruetter et al., Comparison of Relaxation Induced by Glyceryl Trinitrate, Isosorbide Dinirate, and Sodium Nitroprusside in Bovine Airways, *Am. Rev. Respir. Dis.* 139:1192–1197 (1989).

Gryglewski et al., Superoxide anion is involved in the breakdown of endothelium-derived vascular relaxing factor, *Nature* 320:454–456 (1986).

Heaton et al., Topical Glyceryltrinitrate Causes Measurable Penile Arterial Dilation in Impotent Men, *J. Urology* 143:729–731 (1990).

Henry et al., S-nitrosothiols as vasodilators: implications regarding tolerance to nitric oxide-containing vasodilators, *Br. J. Pharmacol.* 98:757–766 (1989).

Holmquist et al., L-$N^G$-nitro arginine inhibits non-adrenergic, non-cholinergic relaxation of human isolated corpus cavernosum, *Acta Physiol. Scand.* 141:441–442 (1991).

Ignarro et al., Nitric Oxide and Cyclic GMP Formation Upon Electrical Field Stimulation Cause Relaxation of Corpus Cavernosum Smooth Muscle, *Biochem. Biophys. Res. Comm.* 170(2):843–850 (1990).

Ignarro et al., Endothelium-derived relaxing factor produced and released from artery and vein is nitric oxide, *Proc. Natl. Acad. Sci. USA* 84:9265–9269 (1987).

Ignarro et al., Mechanism of Vascular Smooth Muscle Relaxation by Organic Nitrates, Nitrites Nitroprusside and Nitric Oxide: Evidence for the . . . , *J. Pharm. Exp. Ther.* 218(3):739–749 (1990).

Ignarro et al., Haem-Dependant Activation of Guanylate Cyclase and Cyclic GMP Formation by endogenous Nitric Oxide: A Unique Transduction . . . , *Pharmacology and Toxicology* 67:1–7 (1990).

Ignarro et al., Biological Actions and Properties of Endothelium-Derived Nitric Oxide Formed and Released From Artery and Vein, *Circulation Research* 65(1):1–21 (1989).

Jeong et al., Effects of Glyceryl Trinitrate on Guinea--Pig Tracheal Smooth Muscle, *Am. Rev. Resp. Dis.* 117:133 (1978).

Katsuki et al., Effects of Sodium Nitroprusside, Nitroglycerin, and Sodium Azide on Levels of cyclic nucleotides and Mechanical Activity of Various Tissues, *J. Cyc. Nuc. Res.* 3:239–247 (1977).

Kishen et al., Some actions of sodium nitroprusside and glyceryl trinitrate on guinea-pig isolated trachealis muscle, *J. Pharm. Pharmacol.* 37:502–504 (1984).

Kowaluk et al., Spontaneous Liberation of Nitric Oxide Cannot Acount for in Vitro Vascular Relaxation by S-Nitrosothiols, *J. Pharm. Exp. Ther.* 255(3):1256–1264 (1990).

Li et al., Nitric oxide and vasoactive intestinal polypeptide mediate non-adrenergic, non-cholinergic inhibitory transmisson to smooth muscle of the rat gastric fundus, *Eur. J. Pharm.* 191:303–309 (1990).

Long et al., Anion exchange resins discriminate between nitric oxide and EDRF *Eur. J. Pharm.* 142:317–318 (1987).

Loscalzo et al., S-Nitrosocaptopril. I. Molecular Characterization and Effects on the Vasculature and on Plants, *J. Pharm. Exp. Ther.* 249(3):726–729 (1989).

(List continued on next page.)

OTHER PUBLICATIONS

Marletta, M. A., Nitric oxide: biosynthesis and biological significance, *TIBS* 14:488–492 (1989).

Morales et al., The medical treatment of impotence: an update, *World J. Urol.* 8:80–83 (1990).

Myers et al., Vasorelaxant properties of the endothelium-derived relaxing factor more closely resemble S-nitrosocysteine than nitric oxide, *Nature* 345:161–163 (1990).

Oae et al., Organic thionitrites and Related Substances. A Review, *Org. Prep. Proc. Int.* 15(3):165–198 (1983).

Palmer et al., Nitric oxide release accounts for the biological activity of endothelium-derived relaxing factor, *Nature* 327:524–526 (1987).

Shikano et al., Differential selectivity of endothelium-derived relaxing factor and nitric oxide in smooth muscle, *Br. J. Pharmac.* 92:483–485 (1987).

Shikano et al., Endothilium-Derived Relaxing Factor is a Selective Relaxant of Vascular Smooth Muscle, *J. Pharm. Exp. Ther.* 243(1):55–60 (1987).

Stamler et al., S-Nitrosylation of proteins with nitric oxide: Synthesis and characterization of biologically active compounds, *Proc. Natl. Acad. Sci. USA* 89:444–448 (1992).

Staritz, M. Pharmacology of the Sphincter of Oddi, *Endoscopy* 20:171–174 (1988).

Suzuki et al., The Relationship Between Tissue Levels of Cyclic GMP and Tracheal Smooth Muscle Relaxation in the Guinea-Pig, *Clin. Exp. Pharm. Physiol.* 13:39–46 (1986).

Vanhoutte, P. M., Epithelium-derived Relaxing Factor(s) and Bronchial Reactivity *Am. Rev. Respir. Dis.* 138:s24–s30 (1988).

Vickers et al., Corpora Cavernosa Ultrastructure in Vascular Erectile Dysfunction, *Journal of Urology* 143:1131–1134 (1990).

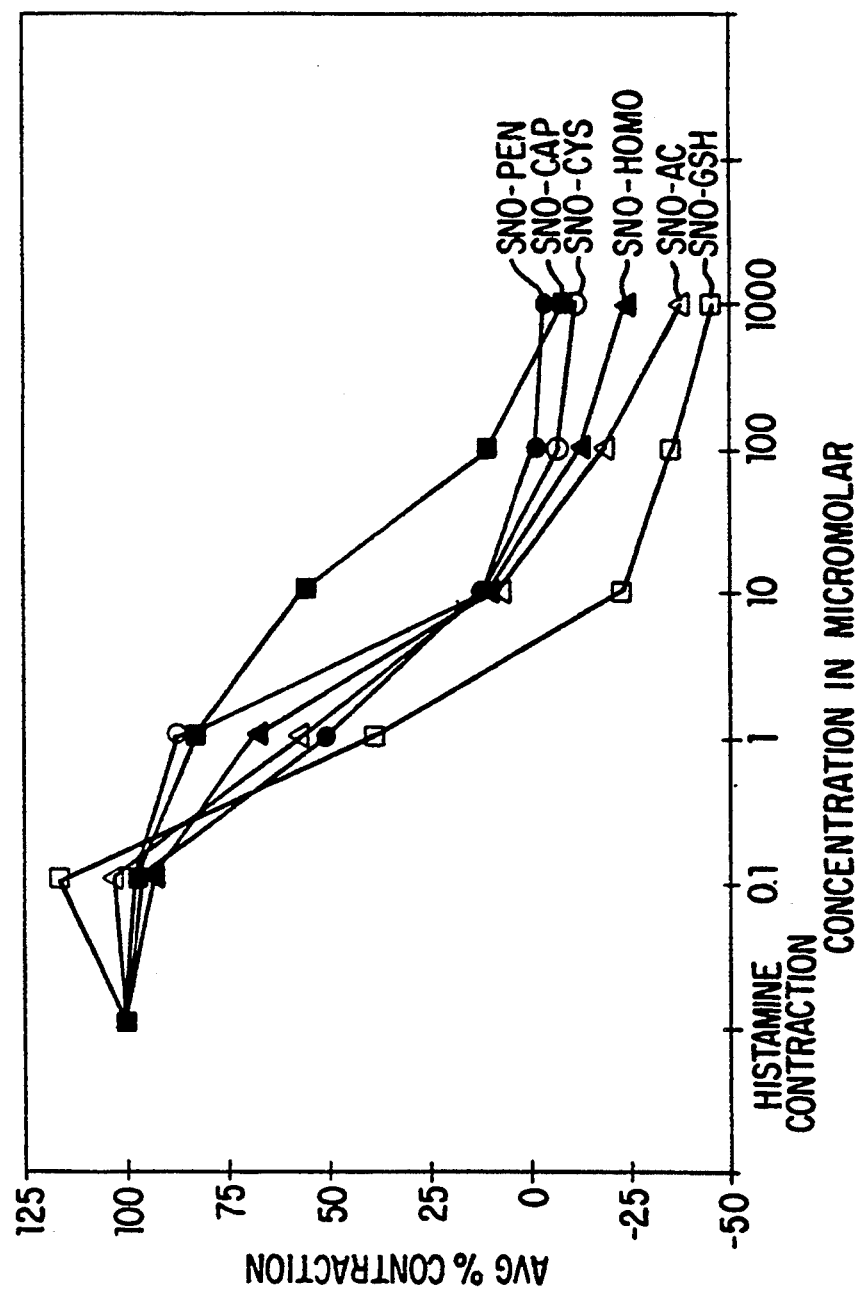

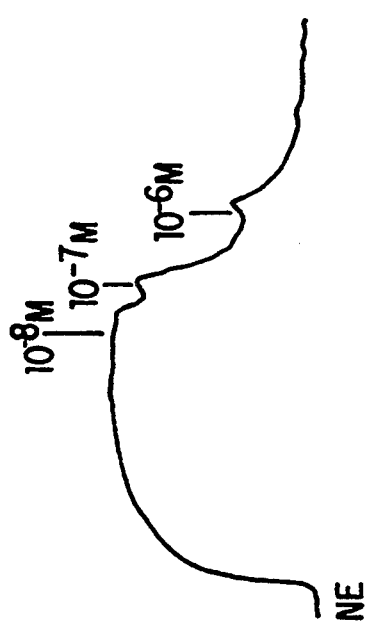
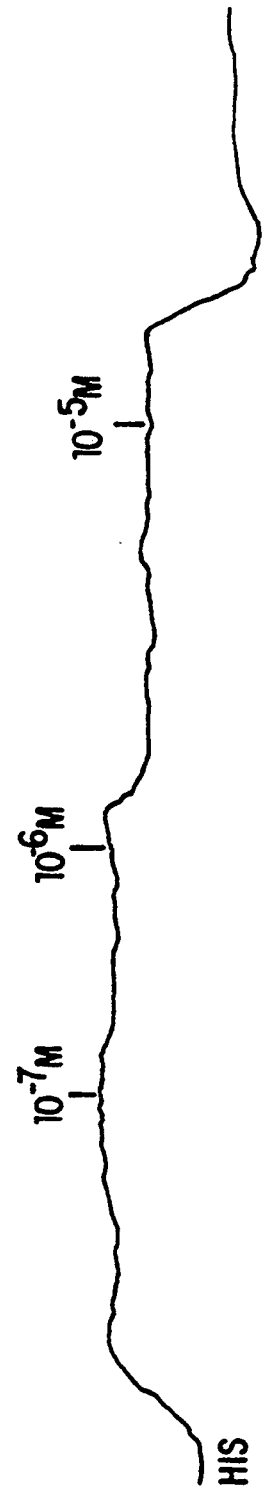
FIG. 7A
FIG. 7B

S-NITROSOTHIOLS AS SMOOTH MUSCLE RELAXANTS AND THERAPEUTIC USES THEREOF

CROSS-REFERENCE TO RELATED APPLICATION

This application is a continuation-in-part of U.S. application Ser. No. 07/804,665, filed Dec. 11, 1992 now abandoned, which is a continuation-in-part of U.S. application Ser. No. 676,691, filed Mar. 29, 1991, abandoned.

BACKGROUND OF THE INVENTION

This invention was made with government support under R01-HL40411, HL43344, and R04870, awarded by The National Institutes of Health. The government has certain rights in the invention.

1. Field of the Invention

This invention relates to the use of low molecular weight S-nitrosothiols, such as S-nitroso-N-acetylcysteine, S-nitroso-glutathione, S-nitroso-homocysteine, S-nitroso-cysteine, S-nitroso-penicillamine and S-nitroso-captopril, to relax non-vascular smooth muscle. Types of smooth muscle include airway, gastrointestinal, bladder uterine, and corpus cavernosum. The invention also relates to the use of S-nitrosothiols for the treatment or prevention of disorders which involve non-vascular smooth muscle, such as respiratory disorders, gastrointestinal disorders, urological dysfunction, impotence, uterine dysfunction or premature labor. The invention also relates to the use of S-nitrosothiols to ameliorate smooth muscle contraction or spasm and thus, facilitate diagnostic or therapeutic procedures, such as bronchoscopy, endoscopy, laparoscopy, and cystoscopy. S-nitrosothiols may also be used to increase hemoglobin-oxygen binding, and thus enhance oxygen transport to bodily tissues.

2. Brief Description of the Background Art

The endothelium secretes a vascular relaxing factor, known as endothelium-derived relaxing factor (EDRF), which has been identified as nitric oxide (NO), or a closely related derivative thereof. (Palmer et al., *Nature* 327: 524-526 (1987); Ignarro et al., *Proc. Natl. Acad. Sci. USA* 84: 9265-9269 (1987)). Under physiologic conditions, however, NO is exceedingly unstable, reacting essentially instantaneously with oxygen, superoxide anion, and redox metals (Lancaster et al., *Proc. Natl. Acad. Sci. USA* 87: 1223-1227 (1990); Ignarro et al., *Circ. Res.* 65: 1-21 (1989); and Gryglewski et al., *Nature* 320: 454-456 (1986)). This fact has lead to the supposition that, in order to exert its effect on vascular smooth muscle, NO must be stabilized in vivo in a form that preserves its biological activity.

S-nitrosothiols (RS-NO) are adducts that form readily under physiologic conditions from the reaction of NO with reduced low molecular weight thiols (Oae et al., *Org. Prep. Proc. Int.* 15(3): 165-198 (1983)). These compounds have half-lives that are significantly greater than that of NO and, like EDRF, possess vasorelaxant activity that is mediated through activation of guanylate cyclase (Kowaluk et al., *J. Pharmacol. Exp. Ther.* 256: 1256-1264 (1990); Loscalzo et al., *J. Pharmacol. Exp. Ther.* 249(3): 726-729 (1989); and Ignarro et al., *J. Pharmacol. Exp. Ther.* 218(3): 739-749 (1981)).

The relaxant effect of S-nitrosothiols on blood vessels, and the mechanism by which this effect is exerted, is reasonably well understood in the art. However, the role of NO, or involvement of the guanylate cyclase pathway in non-vascular smooth muscle is not as clearly understood.

Pulmonary immune responses result in the liberation of cytokines and inflammatory mediators which contribute to the narrowing of airway smooth muscle. As part of this process, pulmonary endothelial cells, macrophages and polymorphonuclear leukocytes are believed to induce nitric oxide synthetase, thus serving as a source of NO. The consequences of NO production in the lung are not known. However, the potential beneficial effects of NO through bronchodilation may be counterbalanced by generation of toxic nitrogen oxides that form readily under the high ambient concentration of oxygen and other reactive oxygen species.

Likewise, introduction of NO into the lungs also results in significant adverse effects, which occur as a direct result of the particular chemical reactivity of the uncharged NO radical (NO.). These adverse effects create impediments to NO therapy which generally involves administration of NO.. For example, the reaction between NO., and $O_2$ or reactive $O_2$ species which are present in high concentrations in the lung, generates highly toxic products, such as $NO_2$ and peroxynitrite. These reactions also result in the rapid inactivation of NO, thus eliminating any beneficial pharmacological effect. (Furchgott R. F. et al., *I. Endothelium-Derived Relaxing Factors and Nitric Oxide*; eds. Rubanyi G. M., pp. 8-21 (1990); Gryglewski, R. J. et al., *Nature* 320: 454-456 (1986)). Furthermore, NO. reacts with the redox metal site on hemoglobin to form methemoglobin, which inhibits oxygen-hemoglobin binding, thereby significantly reducing the oxygen-carrying capacity of the blood.

Non-vascular smooth muscle is present in numerous organ systems throughout the body, and has a vital role in the physiological function of these systems. For example, airway smooth muscle plays a critical role in constriction and dilation of bronchi. In the gastrointestinal tract, the sphincter of Oddi, a smooth muscle connection between the bile duct and duodenum, provides tonic contraction which serves to prevent reflux of duodenal contents into the pancreatic and bile ducts, and promotes filling of the gall bladder. In addition, esophageal (sphincters and body), intestinal and colonic motility is regulated by smooth muscle. Smooth muscle of the bladder body, bladder base, and proximal urethra plays an important role in urological function, and erectile function is mediated by relaxation of corpus cavernosal smooth muscle.

In summary, the relaxation kinetics of non-vascular smooth muscle are very important in numerous physiological systems. Moreover, a variety of significant clinical disorders occur, which involve contraction, spasm, or failure to achieve the necessary relaxation of smooth muscle. Examples of such disorders include airway obstruction (i.e., asthma, bronchitis and emphysema), bladder dysfunction, gastrointestinal muscle spasm (i.e., irritable bowel syndrome, achalasia, dumping disorders), and impotence. Thus, a clinical need exists for pharmacological agents which can treat or prevent such disorders by inducing relaxation of the affected smooth muscle.

SUMMARY OF THE INVENTION

This invention is based on the discovery by the inventors that S-nitrosothiols exert a potent relaxant effect on non-vascular smooth muscle. This concept lead the inventors to the discovery that S-nitrosothiol compounds may be used as a therapeutic modality in disorders which involve smooth muscle relaxation.

The invention is directed to an S-nitrosothiol compound which has the formula:

$$CH_3(CH_2)_xSNO$$

wherein:
X equals 2 to 20.

The invention is also directed to an S-nitrosothiol compound which has the formula:

$$HS(CH_2)_xSNO$$

wherein:
X equals 2 to 20.

The invention is also directed to an S-nitrosothiol compound which has the formula:

$$ONS(CH_2)_xY$$

wherein:
X equals 2 to 20 and Y is selected from the group consisting of fluoro, $C_1$–$C_6$ alkoxy, cyano, carboxamido, $C_3$–$C_6$ cycloalkyl, aralkoxy, $C_2$–$C_6$ alkylsulfinyl, arylthio, $C_1$–$C_6$ alkylamino, $C_2$–$C_{15}$ dialkylamino, hydroxy, carbamoyl, $C_1C_6$ N-alkylcarbamoyl, $C_2$–$C_{15}$ N,N-dialkylcarbamoyl, amino, hydroxyl, carboxyl, hydrogen, nitro and aryl; wherein aryl includes benzyl, naphthyl, and anthracenyl groups.

The invention is also directed to the use of S-nitrosothiols for the treatment or prevention of disorders associated with relaxation of smooth muscle, such as airway obstruction, gastrointestinal spasm, bladder dysfunction and impotence. The invention is also directed to the use of S-nitrosothiols to alleviate smooth muscle contraction and spasm, and thus facilitate procedures involving diagnostic instrumentation such as endoscopy and bronchoscopy.

In particular, this invention is directed to a method for relaxing airway smooth muscle by administering a therapeutically effective amount of an S-nitrosothiol compound to an animal. The S-nitrosothiol compound may be selected from the group consisting of S-nitroso-N-acetylcysteine, S-nitroso-glutathione, S-nitroso-cysteine, S-nitroso-homocysteine, S-nitroso-penicillamine and S-nitroso-captopril. The S-nitrosothiol compound may be selected from the group consisting of a compound having the formula:

$$CH_3(CH_2)_xSNO$$

wherein:
X equals 2 to 20.

The invention is also directed to an S-nitrosothiol compound which has the formula:

$$HS(CH_2)_xSNO$$

wherein:
X equals 2 to 20.

The invention is also directed to an S-nitrosothiol compound which has the formula:

$$ONS(CH_2)_xY$$

wherein:
X equals 2 to 20 and Y is selected from the group consisting of fluoro, $C_1$–$C_6$ alkoxy, cyano, carboxamido, $C_3$–$C_6$ cycloalkyl, aralkoxy, $C_2$–$C_6$ alkylsulfinyl, arylthio, $C_1$–$C_6$ alkylamino, $C_2$–$C_{15}$ dialkylamino, hydroxy, carbomoyl, $C_1C_6$ N-alkylcarbamoyl, $C_2$–$C_{15}$ N,N-dialkylcarbamoyl, amino, hydroxyl, carboxyl, hydrogen, nitro and aryl; wherein aryl includes benzyl, naphthyl, and anthracenyl groups.

The invention is also directed to a method for treatment or prevention of respiratory disorders by administering a therapeutically effective amount of S-nitrosothiol compound to an animal. Respiratory disorders include obstructive lung disease, emphysema, asthma, bronchitis, fibrosis, excessive mucus secretion, obstruction or air flow, and lung disorders resulting from post-surgical complications.

The invention is also directed to a method for relaxing gastrointestinal smooth muscle by administering a therapeutically effective amount of an S-nitrosothiol compound to an animal.

The invention is also directed to a method for ameliorating contraction or spasm of gastrointestinal smooth muscle associated with endoscopic procedures, by administering a therapeutically effective amount of an S-nitrosothiol compound to an animal.

The invention is also directed to a method for relaxing corpus cavernosum smooth muscle by administering a therapeutically effective amount of an S-nitrosothiol compound to an animal.

The invention is directed to a method for the treatment or prevention of impotence by administering a therapeutically effective amount of an S-nitrosothiol compound to an animal.

The invention is also directed to a method for relaxing bladder smooth muscle by administering a therapeutically effective amount of an S-nitrosothiol compound to an animal.

The invention is also directed to a method for relaxing uterine smooth muscle by administering a therapeutically effective amount of an S-nitrosothiol compound to an animal.

The invention is also directed to the administration of said S-nitrosothiol compounds for the methods of the invention, as part of the pharmaceutical composition comprising a pharmaceutically acceptable carrier.

The invention is also directed to the methods of the invention wherein the pharmaceutical composition containing the S-nitrosothiol compound is administered to an animal by a route comprising oral, sublingual, intravenous, topical, intramuscular or intranasal delivery.

The invention is also directed to a method for increasing the capacity of hemoglobin to bind oxygen, comprising administering a therapeutically effective amount of an S-nitrosothiol compound to an animal in need thereof.

The invention is also directed to a method for increasing oxygen transport to bodily tissues, comprising administering a therapeutically effective amount of an S-nitrosothiol compound to an animal in need thereof.

The invention is also directed to a method for the treatment or prevention of disorders associated with insufficient oxygen supply to bodily tissues, comprising administering a therapeutically effective amount of an S-nitrosothiol to an animal in need thereof.

BRIEF DESCRIPTION OF THE FIGURES

FIG. 3: Side-by-side comparison of the relaxant effect of specific S-nitrosothiols on guinea pig tracheal muscle.

FIG. 7: The relaxation response to S-nitroso-glutathione in guinea pig airway (A) and rabbit aorta (B).

DESCRIPTION OF THE PREFERRED EMBODIMENTS

Figure 1:
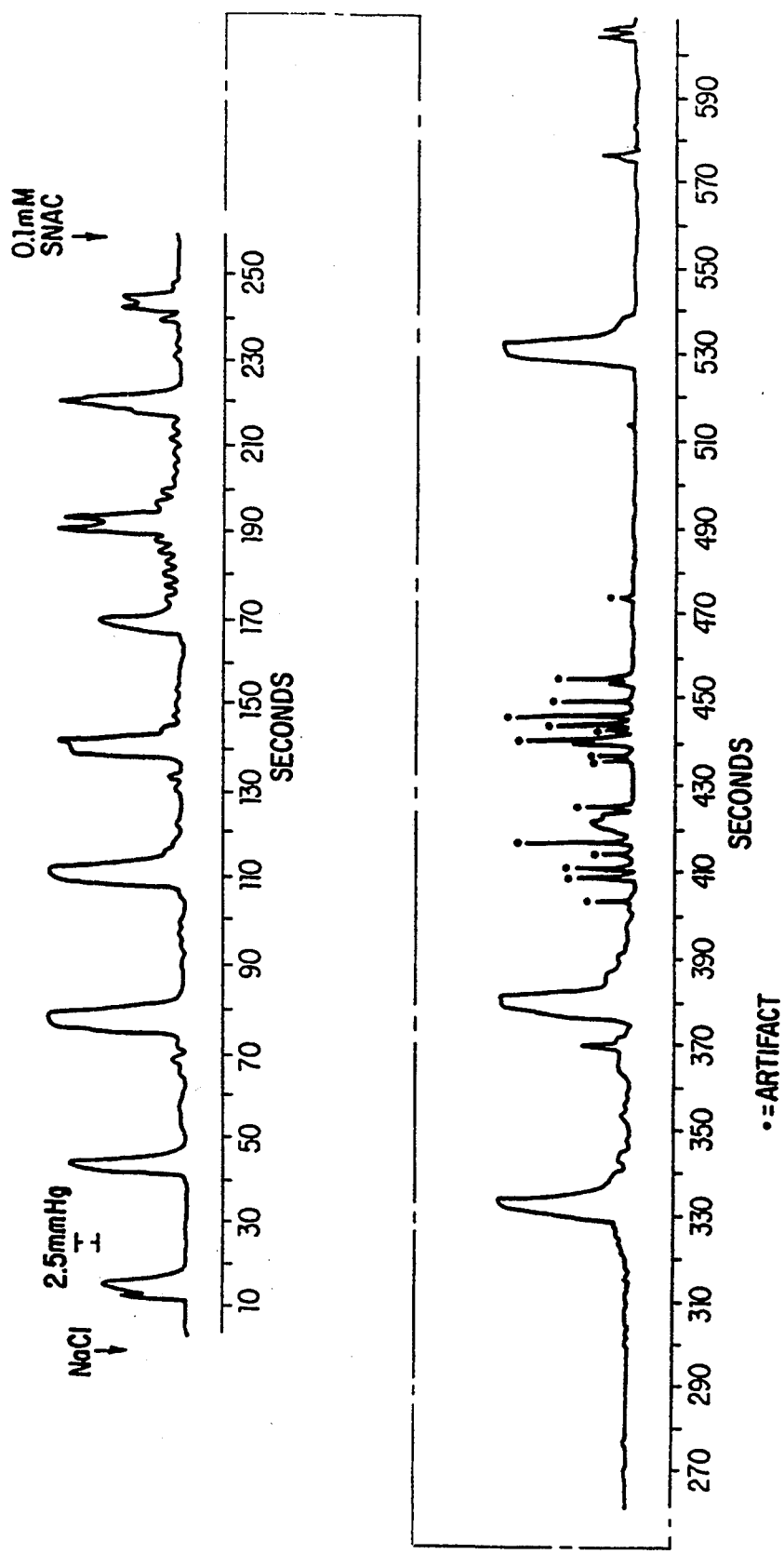
FIG. 1: Inhibition of the Sphincter of Oddi by administration of S-nitroso-N-acetylcysteine.

The invention is based on the discovery by the inventors that S-nitrosothiols relax non-vascular smooth muscle, and possess unique and different relaxant activities, kinetic properties and membrane permeability, and thus, may be used to treat or prevent disorders which involve non-vascular smooth muscle.

In one embodiment, the term "S-nitrosothiol" refers to a compound which is selected from the group consisting of S-nitroso-N-acetylcysteine, S-nitroso-glutathione, S-nitroso-cysteine, S-nitroso-homocysteine, S-nitroso-pantathoeine derivatives, S-nitroso-penicillamine and S-nitroso-captopril.

In another embodiment the term "S-nitrosothiol" refers to particular novel S-nitrosothiol compounds synthesized by the inventors, for use as smooth muscle relaxants. The compounds represented by the general formula of $CH_3(CH_2)_xSNO$ are long carbon-chain lipophilic nitrosothiols. The compounds represented by the general formula of $HS(CH_2)_xSNO$ are S-nitrosodithiols, possessing an additional thiol group. The compounds represented by the general formula of $ONS(CH_2)_xY$ are S-nitrosothiols which possess other functional groups, in addition to the thiol.

The invention is related to the discovery that S-nitrosothiol compounds relax non-vascular smooth muscle. As a result, these compounds may be used to treat or prevent those pathophysiologic conditions which result from, or involve, constriction of smooth muscle, or those which necessitate therapeutic intervention to achieve smooth muscle relaxation.

One embodiment of the invention relates to the administration of a therapeutically effective amount of an S-nitrosothiol to an animal to relax airway smooth muscle. The term "airway smooth muscle" refers to the smooth muscle lining the bronchi or tracheal region. The inventors have demonstrated that S-nitrosothiols exert a potent relaxant effect upon airway smooth muscle.

As a result of this potent relaxant effect exerted by S-nitrosothiols, these compounds may be administered as therapeutic agents for the treatment or prevention of respiratory disorders.

The term "respiratory disorder" refers to any impairment of lung function which involves constriction of airways and changes in blood gas levels or lung function.

For example, airway obstruction constitutes a respiratory disorder which occurs as a result of acute pulmonary impairment or obstructive lung disease. Severe airway obstruction may ultimately result in life-threatening respiratory failure. Airway obstruction occurs in patients with chronic obstructive lung diseases, such as emphysema and bronchitis. These patients often experience recurrent episodes of respiratory failure as a result of severe airway obstruction. Emphysema can result in significant disability due to dyspnea, extreme restriction of physical activity, and mortality.

Airway obstruction also results from asthma, a disorder characterized by increased responsiveness of the tracheobronchial tree to various stimuli, and which leads to generalized airway constriction manifested by dyspnea, cough and wheezing. Asthma sufferers often experience acute exacerbations of bronchoconstriction, which may be life-threatening.

Another obstructive lung disease, cystic fibrosis, results from abnormal exocrine gland function. Clinical manifestations include excessive mucous secretion, hypertrophy of bronchial glands, infection, and inflammatory and structural changes in the airways which lead to obstruction and ventilation-perfusion imbalance.

Acute respiratory failure may result not only from obstructive disease, but also as a consequence of airway constriction secondary to pneumonia, thromboembolism, left ventricular failure and pneumothorax. Acute respiratory failure may also result from ventilation-perfusion imbalance.

A critical component in the treatment of airway obstruction involves the use of pharmacologic agents to remove secretions and reverse airway constriction. The most commonly used bronchodilatory agents are beta-agonists, such as isoproterenol, given by inhalation or subcutaneous injection, and methylxanthines, such as theophylline, given orally or by infusion.

The margin of safety for theophylline administration is relatively narrow. The minimum therapeutic concentration in plasma is 6 to 10 μg/ml, and unacceptable symptoms of toxicity usually appear at or above 20 μg/ml. Still higher concentrations can lead to serious central nervous system toxicity, with long-term ingestion of theophylline being a predisposing factor in such toxicity. Moreover, because the clearance of theophylline is influenced by genetic, developmental and environmental factors to a significant degree, it is necessary to titrate the dosage cautiously against clinical observations of beneficial or toxic effects, with periodic determination of the concentration of the drug in plasma (Gilman A. G., The Pharmacological Basis of Therapeutics, Pergamon Press, New York, (1990)).

Isoproterenol, a non-selective β-agonist, produces cardiovascular side effects such as palpitations, sinus tachycardia and more serious arrhythmias. In addition, tolerance to this drug may result from overuse (Gilman A. G., The Pharmacological Basis of Therapeutics, Pergamon Press, New York, (1990)). This characteristic reduces its usefulness in patients with chronic obstructive disease who rely heavily on frequent use of bronchodilators. It has now been demonstrated that β agonists may have long term deleterious effects which result in aggravation of asthma, and ultimately change the natural history of the disease. Consequently, the American Thoracic Society no longer recommends treatment with β agonists as first line therapy in mild asthma (Expert Panel Recommendation, New England Journal of Medicine, 325: 425-426 (1991)).

The use of S-nitrosothiols for the treatment of airway obstruction provides significant advantages over current methods of treatment. The use of S-nitrosothiols eliminates the untoward side effects associated with β-agonists and methylxanthines. S-nitrosothiols also potently inhibit platelets and neutrophils which have been implicated in the pathogenesis of asthma.

Furthermore, because all current treatment methods act by way of cAMP, S-nitrosothiols satisfy the need for bronchodilators which act by way of cGMP. This is important because current evidence provided by the inventors demonstrates a role for cyclic GMP in regulation of airway tone in humans (See Example 1). In addition, cyclic GMP agonists act synergistically with cyclic AMP agonists to provide bronchodilation, not obtainable by individual agents.

The inventors have also demonstrated that S-nitrosothiols also cause relaxation of smooth muscle by a cGMP-independent mechanism. Another mechanism by which bronchodilation is effected provides an opportunity for combination therapy, because the independent mechanisms have potential for synergy.

A significant advantage of S-nitrosothiols is that they deliver NO in its most biologically relevant, and non-toxic form. This is critical, because the pharmacological efficacy of NO, particularly in airways, depends upon the form in which it is delivered. As demonstrated by the inventors, S-nitrosothiols can deliver NO as charged species, nitrosonium (NO+) or nitroxyl (NO−), as opposed to the uncharged NO radical (NO.). This is important because the charged species behave in a very different manner from NO. with respect to chemical reactivity.

In contrast to NO., nitrosonium and nitroxyl do not react with $O_2$ or $O_2$ species to produce toxic oxides of nitrogen, and are also resistant to decomposition in the presence of redox metals. Consequently, administration of these NO equivalents does not result in the generation of toxic by-products, or elimination of the active NO moiety. Thus, by delivering nitrosonium or nitroxyl, S-nitrosothiols provide a means for achieving the smooth muscle relaxant effects of NO, and at the same time, alleviate significant adverse effects previously associated with NO therapy. S-nitrosothiols may also be used as a means to deliver free NO in a stable and non-toxic form, for use in free NO therapy.

In addition, to causing bronchodilation, S-nitrosothiols may also be used to increase the oxygen-binding capacity of hemoglobin. Hemoglobin is a globular protein, which binds reversibly to blood oxygen through passive diffusion from entry of air into the lungs. Hemoglobin-oxygen binding greatly increases the capacity of the blood to transport oxygen to bodily tissues; thus, the binding affinity between hemoglobin and oxygen is a critical factor in determining the level of oxygen transport to the tissues. The inventors have demonstrated that S-nitrosothiols do not react with the iron-binding site of hemoglobin, as does NO., but instead, bind to the thiol group. Thus, methemoglobin formation is prevented and hemoglobin-oxygen binding is unimpaired.

Furthermore, the inventors have also demonstrated that S-nitrosothiols not only prevent impairment, of binding, but actually increase hemoglobin-oxygen binding. Therefore, S-nitrosothiols may be used to increase the oxygen-carrying capacity of the blood, and oxygen transport to bodily tissues. As a result, these compounds may be useful in the treatment of disorders which are associated with insufficient oxygen transport, or in clinical situations in which increased oxygen transport is needed. Examples of such clinical situations include, but are not limited to, hypoxic disorders resulting from pneumothorax, airway obstruction, paralysis or weakness of the respiratory muscles, inhibition of respiratory centers by drugs or other agents, or other instances of decreased pulmonary ventilation. Additional clinical indications include impaired alveolar gas diffusion such as occurs in interstitial fibrosis, bronchiole constriction, pulmonary edema, pneumonia, hemorrhage, drowning, anemias, arteriovenous shunts.

Finally, the inventors have demonstrated that S-nitrosothiols mediate the activity of vasoactive intestinal peptide (VIP), an important airway relaxant. This reinforces the importance of S-nitrosothiols in regulation of airway tone. Deficiency in the effect of VIP is a causal factor in the pathogenesis of asthma. Administration of S-nitrosothiols replenishes the mediator itself rather than a less biologically active derivative.

S-nitrosothiols are also suitable for direct instillation into the lungs by bronchoscopic means. This topical administration permits titration of dose, eliminates the untoward side effects of systemic therapy, and enables the use of combination therapy, involving a topical S-nitrosothiol in conjunction with a systemic agent, in problematic cases. This topical therapy would also facilitate endoscopy by suppressing the cough reflex and associated bronchospasm.

An important component in the treatment of airway obstruction is the removal of airway mucous. Thus, airway obstruction often necessitates the administration of a mucolytic agent in conjunction with the bronchodilator. N-acetylcysteine, more commonly known as "Mucomist", is one such agent. S-nitroso-N-acetylcysteine, a particular S-nitrosothiol, is advantageous because it possesses both mucolytic and bronchodilator capabilities.

With respect to combined bronchodilator-mucolytic agents, the mucolytic activity of the compound depends upon the amount of thiol which is preserved after NO delivery. Thus, S-nitrosothiol compounds which contain more than one thiol (dithiol compounds) are particularly suitable for achieving mucolysis. In addition, the long-chain lipophilic S-nitrosothiols which contain more than one thiol are advantageous as mucolytic agents because they have a free thiol, and their lipophilic property facilitates penetration of the compound into the lipid portion responsible for the tenacious viscosity of mucuous.

In addition to the treatment or prevention of respiratory disorders, S-nitrosothiols may also be used to facilitate diagnostic and therapeutic bronchoscopy. The term "bronchoscopy" refers to the procedure in which a flexible fiberoptic, or rigid bronchoscope is introduced into the tracheobronchial tree for the purpose of bronchial visualization, lung biopsy or brushings, aspiration of secretions, and delivery of pharmacological agents.

A complication of bronchoscopy, and thus an impediment to the successful completion of the procedure, is bronchospasm. Patients with a prior history of bronchospasm are particularly at risk for acute enhancement of spasm. Thus, S-nitrosothiols may also be used to relax airway smooth muscle and eliminate bronchoscopy-induced bronchospasm.

Another embodiment of the invention relates to the administration of a therapeutically effective amount of an S-nitrosothiol compound to an animal to relax gastrointestinal smooth muscle. The term "gastrointestinal smooth muscle" refers to smooth muscle which is contained in all areas of the gastrointestinal tract. Such areas include, but are not limited to, the esophagus, duodenum, sphincter of Oddi, biliary tract, ileum, sigmoid colon, pancreatic duct and common bile duct. S-nitrosothiols may be used for the treatment or prevention of gastrointestinal disorders. Disorders of the gastrointestinal tract include achalasia (spasm of the lower esophageal sphincter), diarrhea, dumping syndrome, and irritable bowel.

An additional embodiment of the invention relates to the administration of S-nitrosothiols to alleviate contraction or spasm of gastrointestinal smooth muscle, and thus facilitate successful completion of endoscopic procedures. Contraction or spasm of gastrointestinal smooth muscle imposes a technical obstacle which must frequently be overcome in order to enable the clinician to successfully perform endoscopic procedures.

The term "endoscopic procedures" refers to those diagnostic procedures which utilize an instrument which is introduced into the gastrointestinal tract to provide direct visualization of the gastrointestinal tract, for examination and therapeutic purposes. Such purposes include direct visualization, biopsy, access to the common bile duct, fluid aspiration and removal of foreign bodies, polyps, and other lesions. An example of a particular endoscopic procedure is esophagogastroduodenoscopy, which is utilized for examination of the esophageal lumen, stomach and duodenum. Another example, endoscopic retrograde cholangiopancreatography (ERCP), enables visualization of the pancreatic duct, common bile duct and the entire biliary tract, including the gall bladder. Further examples of endoscopic procedures are colonoscopy and sigmoidoscopy.

Current methods for alleviating gastrointestinal muscle spasm include the administration of intravenous diazepam, anticholinergics and glucagon, as well as sublingual administration of nitroglycerin. However, these methods produce generalized, systemic effects which persist for a much longer duration than the procedure itself. In addition, nitroglycerin is significantly less effective as a smooth muscle relaxant than S-nitrosothiols, and produces systemic side effects, the most significant of which is hypotension. It is therefore, not used clinically. Clearly, a need exists for a topical smooth muscle relaxant which could be directly instilled into the various regions of the gastrointestinal tract to facilitate both diagnostic and therapeutic endoscopic procedures.

Figure 2:
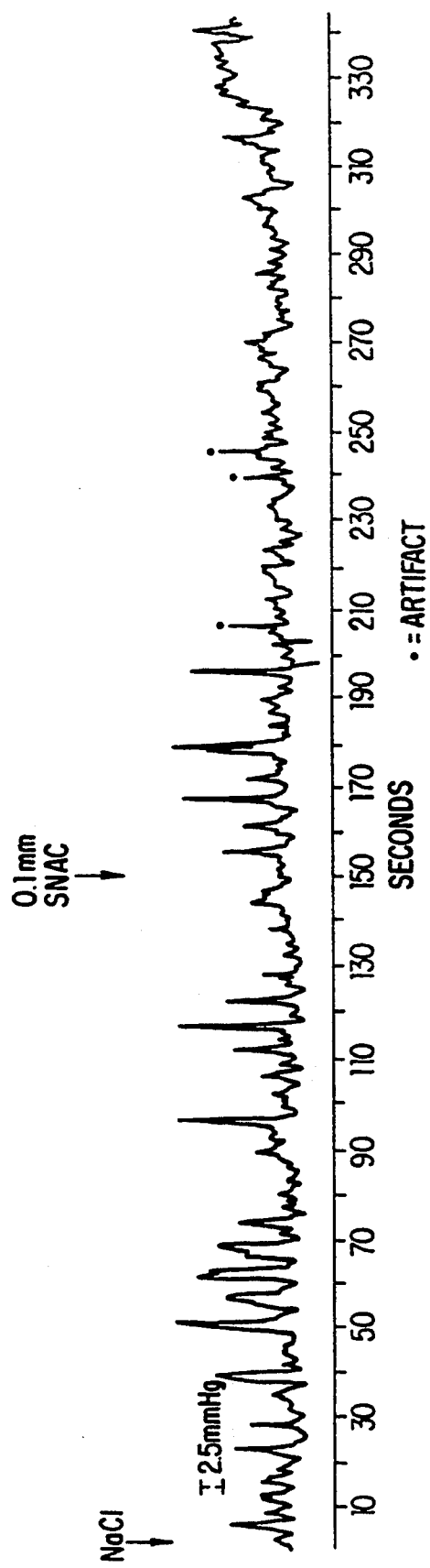
FIG. 2: Inhibition of duodenal motility by administration of S-nitroso-N-acetylcysteine.
Figure 4A:
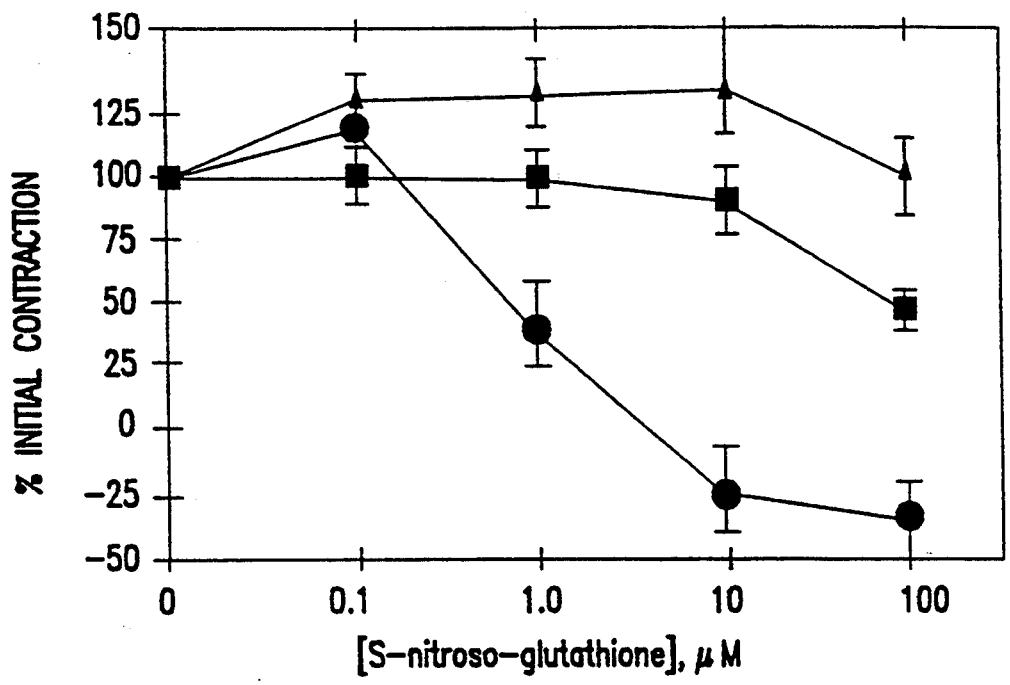
FIG. 4: Dose-dependent relaxant effect of specific S-nitrosothiols on guinea pig tracheal muscle contracted with 3 µM, as compared to the reactant and NO.
 a: S-nitroso-glutathione
 b: S-nitroso-cysteine
 c: S-nitroso-homocysteine
 d: S-nitroso-N-acetylcysteine
 e: S-nitroso-penicillamine
 f: S-nitroso-captopril
Figure 4B:
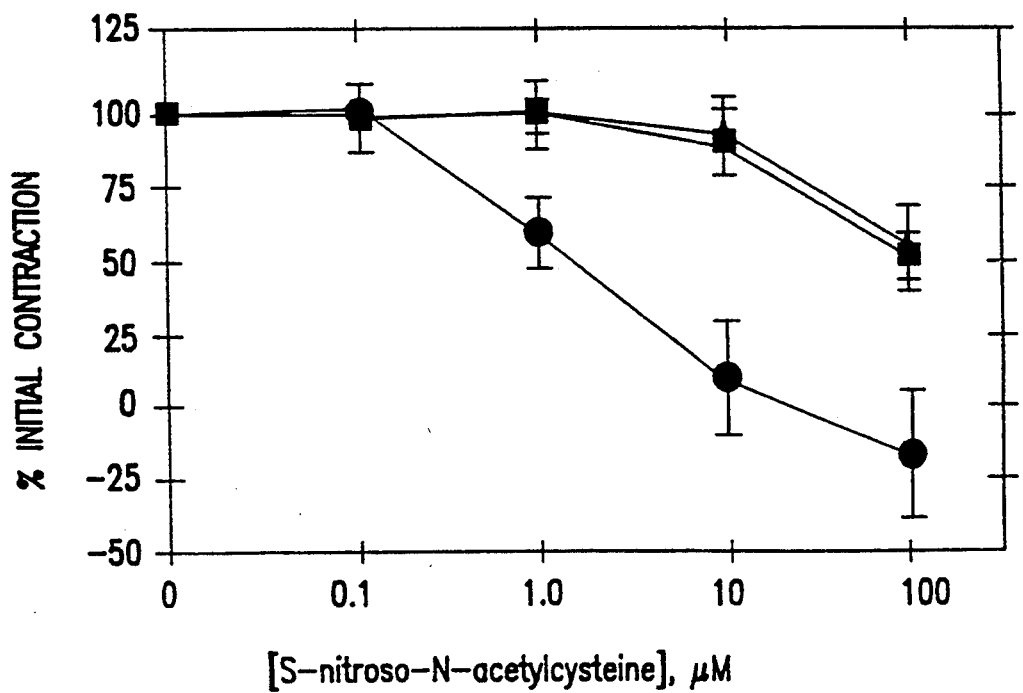
Figure 4C:
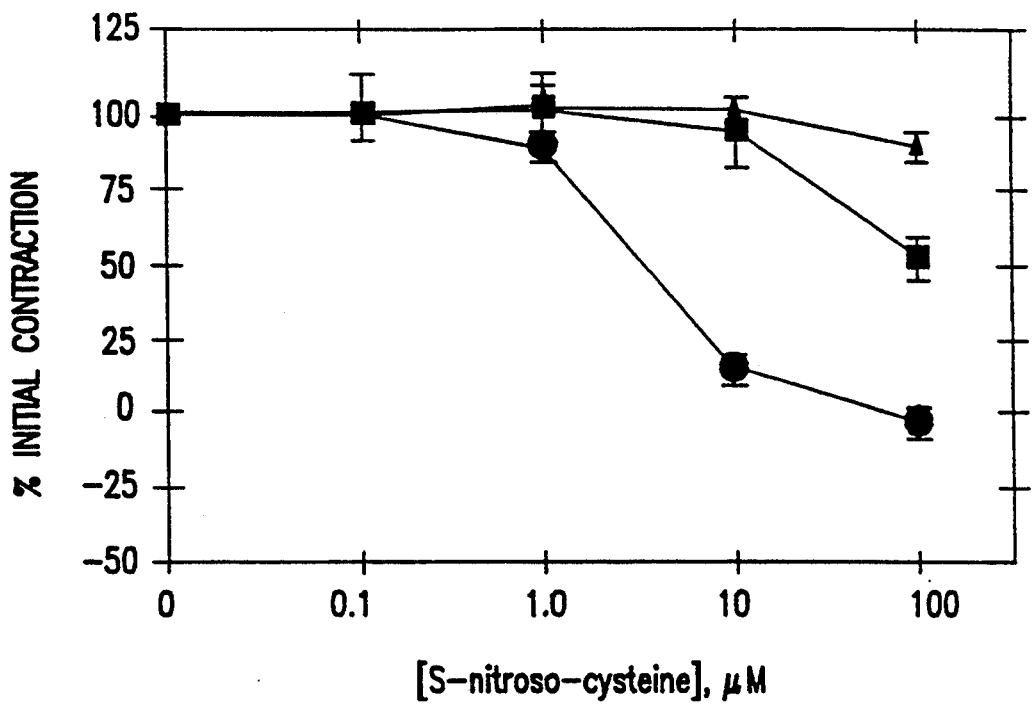
Figure 4D:
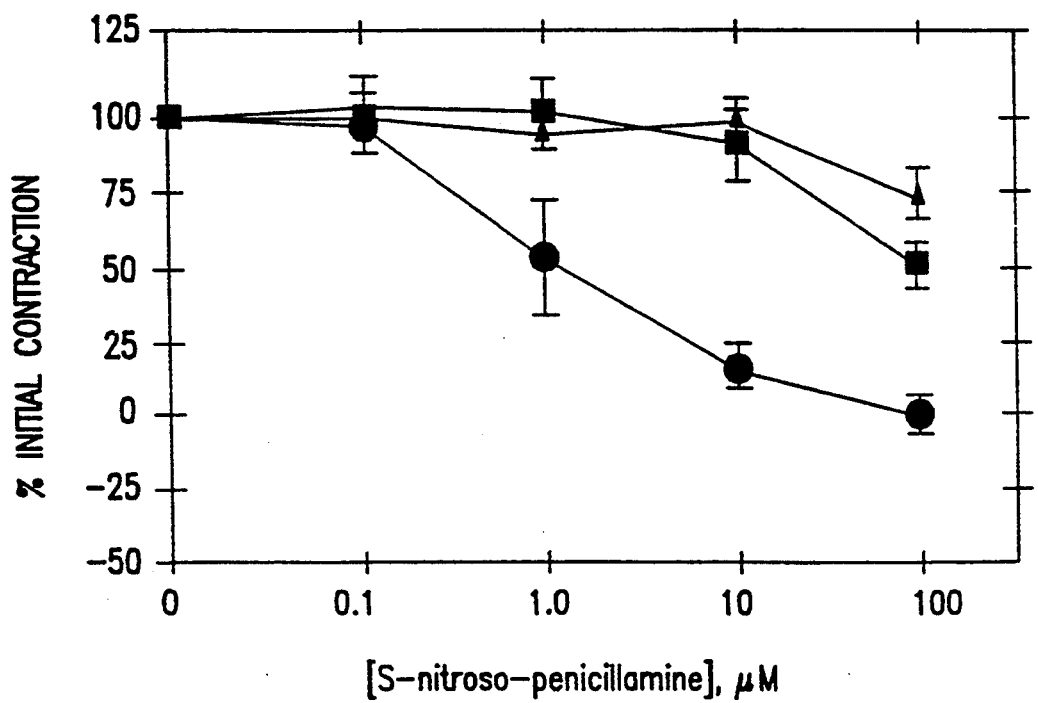
Figure 4E:
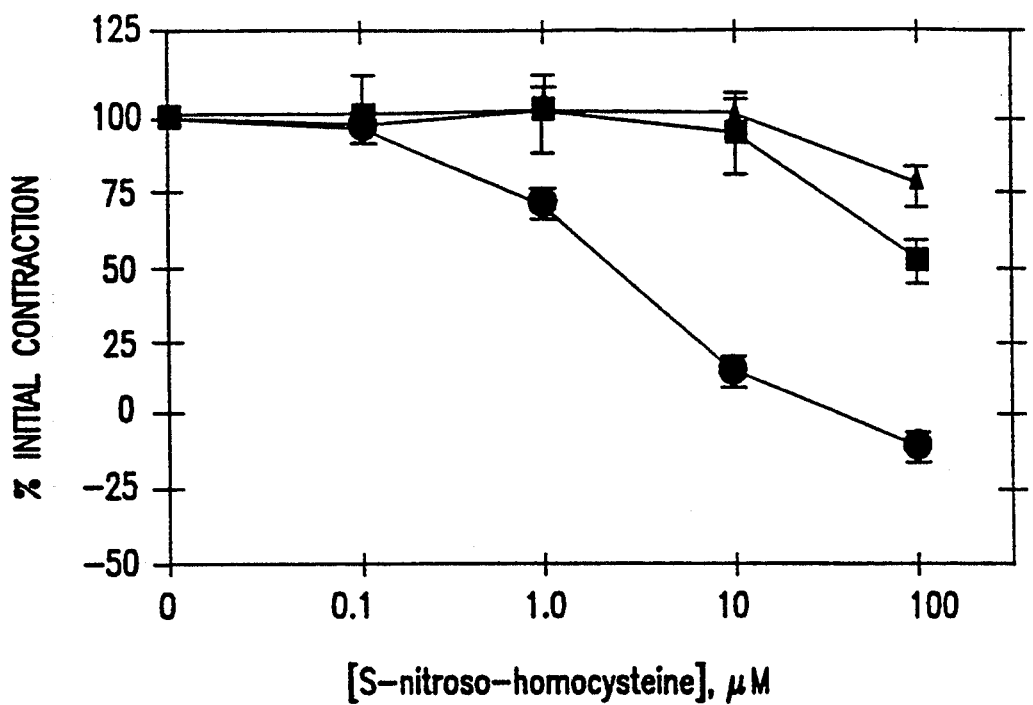
Figure 4F:
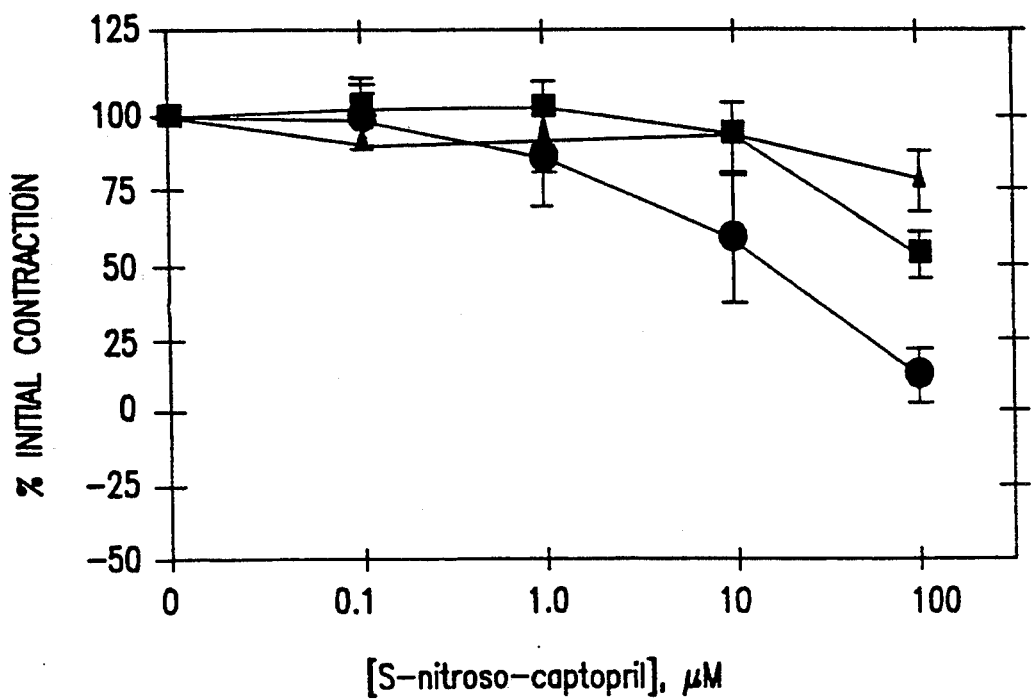

Patient studies, conducted by the inventors, have measured the efficacy of S-nitrosothiols both in facilitating cannulation of the sphincter of Oddi, and in decreasing colon motility to allow for removal of colon polyps. As shown in FIG. 1, topical administration of S-nitroso-N-acetylcysteine eliminated duodenal motility. As shown in FIG. 2, topical administration of S-nitroso-N-acetylcysteine inhibited the contractile activity of the Sphincter of Oddi, and thus, permitting successful endoscopic cannulation of the sphincter. In addition, administration of S-nitroso-N-acetylcysteine eliminated colon motility to facilitate successful removal of colon polyps. Notably, the relaxant effects were temporary (lasting only for the duration of the procedure), completely reversible and produced no change in systemic blood pressure, heart rate or oxygen saturation. The same type of effects would occur with the use of other cell impermeable S-nitrosothiols, such as S-nitroso-glutathione.

Prior to the present invention, there were no available pharmacological agents which could be applied directly by endoscopic means to exert a direct, immediate, localized, and completely reversible relaxant effect on gastrointestinal smooth muscle. Topical administration of S-nitrosothiols, during endoscopy, eliminates systemic side effects and allows for the use of the lowest effective concentration of the drug.

Administration of S-nitrosothiols obviates the need for sphincterotomy, a procedure which substantially increases the morbidity and mortality of ERCP. In addition, administration of S-nitrosothiols aids in the cannulation and manipulation of the pancreatic duct and biliary tract during therapeutic procedures such as gall bladder cannulation, bile duct stone removal and stint placement, and decreases the incidence of post-ERCP complications, such as pancreatis and cholangitis. Another use of S-nitrosothiols involves the intraoperative injection of these compounds into the gall bladder prior to cholecystectomy to alleviate cystic duct spasm. This would allow for a laparoscopic cholangiogram by providing access to the cystic duct. In addition to the uses discussed above, S-nitrosothiols may also be administered to treat or prevent any other technical problems associated with endoscopy which are known to those in the medical art.

Another embodiment of the invention relates to administration of a therapeutically effective amount of an S-nitrosothiol compound to relax corpus cavernosum smooth muscle. The term "corpus cavernosum" refers to two areas of smooth muscle which lie side by side on the dorsal aspect of the penis, and together with the corpus spongeosum that surrounds the urethra, constitute erectile tissue. This erectile tissue consists of an irregular sponge-like system of vascular spaces interspersed between arteries and veins. Erection occurs when cavernosa smooth muscle relaxation causes a decease in arterial resistance and resulting increase in arterial blood flow to the penis.

Smooth muscle has a critical role in erectile function Thus, another embodiment of the invention relates to the administration of a therapeutically effective amount of an S-nitrosothiol compound for the treatment of impotence. "Impotence" refers to a condition of male sexual dysfunction which is characterized by the inability to obtain or maintain an erection.

Organic causes of erectile impotence, may include endocrine, drug-induced, local injury, neurologic, and vascular. In particular, impotence may result from neurologic blockade caused by such drugs as antihistamines, antihypertensives, psychogenic agents, and anticholinergics. Impotence may also result from neurologic disorders such as interior temporal lobe lesions, spinal cord disorders, and insufficiency of sensory input resulting from diabetic neuropathy. An additional cause of impotence is insufficient blood flow into the vascular network resulting from an intrinsic defect, or from penile trauma.

Currently available methods for treating impotence consist largely of surgical techniques and intracavernosal injections of pharmacological agents. One surgical technique involves the implantation of a penile prosthesis by inserting within the corpora, a small silastic rod. However, this method does not produce full erection and the complication rate is high. Alternatively, an inflatable prosthetic device may be implanted on either side of the corpora, with a connecting reservoir of material placed in the perivascular space. Erection is achieved through the use of pumps which are located in the scrotum.

Intracavernous injection of the smooth muscle relaxant, papaverine has been used to induce erections. However, a significant disadvantage of this treatment method is the need for a painful injection each time an erection is desired. In addition, numerous side effects and complications result from the chronic use of drugs such as papaverine. Clinical reports indicate that a significant proportion of potential candidates refuse these injections from the onset of treatment. A larger number of patients, even after favorable initial response to the treatment, become increasingly unresponsive or unwilling to continue injections as a means of treatment (Morales et al., *World J. Urol.* 8: 80–83 (1990)).

In general, a significant number of patients who are potential candidates for current methods of impotence treatment refuse initially because of the invasive nature of the treatment, or reject further treatment because of pain, fibrosis, or dissatisfaction with results.

As demonstrated by the discussion above, prior to the present invention, there was a significant need for a less invasive approach to the treatment of impotence. Because they exert a relaxant effect on corpus cavernosal smooth muscle, S-nitrosothiols are particularly well suited for the treatment of impotence.

Administration of S-nitrosothiols results in relaxation of corpus cavernosum smooth muscle, which leads to dilation of the cavernosal arteries and a concommittent increase in blood flow. S-nitrosothiols provide significant advantages in the treatment of impotence over current treatment methods, because they can be administered topically, thereby eliminating the systemic side effects, significant discomfort, fibrosis, and ineffectiveness associated with the currently available, invasive methods of treatment.

Another embodiment of the claimed invention relates to the administration of a therapeutically effective amount of an S-nitrosothiol compound to relax bladder smooth muscle. Bladder smooth muscle includes that of the bladder base, bladder body and proximal urethra. In addition, S-nitrosothiols may be used for the treatment of bladder dysfunction disorders which involve relaxation of bladder smooth muscle. Such disorders include, but are not limited to, problems with bladder filling, volume and continence.

In addition, S-nitrosothiols may be administered to cause relaxation of urethral and bladder base smooth muscle, and thus, facilitate cystoscopic examination of the urinary tract. The term "cystoscopic examination" refers to the introduction of a fiberoptic instrument through the urethra and into the bladder, to achieve visualization of the interior of the urethra and bladder for diagnostic and therapeutic purposes.

Another embodiment of the invention relates to the administration of a therapeutically effective amount of an S-nitrosothiol compound to relax uterine smooth muscle. Increased contractility of uterine smooth muscle precipitates premature labor. Thus, an additional embodiment of the invention relates to the administration of S-nitrosothiol compounds for the treatment or prevention of premature labor.

S-nitrosothiols may also be used to relax fallopian tube smooth muscle. Fallopian tube smooth muscle plays a role in the transport of the egg to the uterus. Thus, S-nitrosothiols may be used to regulate ovum transport, or to facilitate laparoscopic examination of the fallopian tubes, or to facilitate fertilization procedures.

The long-chain lipophilic compounds have unique potential for NO delivery by incorporation into cell membranes, and for accessing the central nervous system (CNS). In the CNS, nitric oxide has been shown to inhibit cell death resulting from ischemic injury, as well as to possess neurotransmitter functions. Membrane permeability achieved by these compounds also provides the unique potential for NO delivery in every organ system. In addition, NO delivery can be regulated by the incorporation of additional functional groups into the molecule. Each functional group, including but not limited to nitrite, nitrate, redox metal, amine, aromatic, and basic amino acids, has its own unique functional aspects which will affect (a) a targeted site of delivery (b) rate of NO release (c) lipophilicity (d) cell permeability (e) duration of action (f) bioactivity and (g) nitrosation potential.

An additional embodiment of the invention relates to the administration of an S-nitrosothiol compound as part of a pharmaceutical composition, comprising a pharmaceutically acceptable carrier, to achieve the physiological effects discussed above.

The pharmaceutical compositions utilized in this invention can be administered by intranasal, oral, enteral, topical, sublingual, rectal, intramuscular, intravenous, or subcutaneous means. The compositions may be administered by medical instrumentation including, but not limited to, bronchoscopic, endoscopic, laporascopic, and cystoscopic means. With respect to the administration of these composition for the treatment of impotence, the term "topical" includes administration in the form of a condom which contains the pharmaceutical composition. Certain S-nitrosothiols, such as lipophilic S-nitrosothiols, are especially suitable for (i.e. lipophilic) incorporation into the condom itself, to provide sustained release of the compound.

The compounds of this invention can be employed in combination with conventional excipients; i.e., pharmaceutically acceptable organic or inorganic carrier substances suitable for parenteral, enteral or intranasal application which do not deleteriously react with the active compounds. Suitable pharmaceutically acceptable carriers include, but are not limited to, water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, etc. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds.

For parenteral application, particularly suitable vehicles consist of solutions, preferably oily or aqueous solutions, as well as suspensions, emulsions, or implants, including suppositories. Ampules are convenient unit dosages.

For enteral application, particularly suitable are tablets, dragees or capsules having talc and/or a carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

It will be appreciated that the actually preferred amounts of active compounds used will vary according to the specific compound being utilized, the particular compositions formulated, the mode of application and the particular site of administration. Optimal administration rates for a given protocol of administration can be readily ascertained by those skilled in the art, using conventional dosage determination tests conducted with regard to the foregoing guidelines.

According to the present invention, a "therapeutically effective amount" of a pharmaceutical composition is an amount which is sufficient to achieve the desired pharmacological effect. Generally, the dosage required to provide an effective amount of the composition, and which can be adjusted by one of ordinary skill in the art, will vary, depending upon the age, health, physical condition, sex, weight and extent of disease, of the recipient. Additionally, the dosage may be determined by the frequency of treatment and the nature and scope of the desired effect.

Without further elaboration, it is believed that one skilled in the art can, using the preceding description, utilize the present invention to its fullest extent. The following examples are, therefore, to be construed as merely illustrative, and not limitative of the remainder of the disclosure in any way whatsoever.

The entire text of all publications cited above and below are hereby incorporated by reference.

EXAMPLES

Example 1

Airway Smooth Muscle Relaxation by S-nitrosothiols

A. Methods

1. Materials

Glutathione, L-cysteine, DL-homocysteine, D-penicillin, hemoglobin (bovine), methylene blue and Medium 199 sets were purchased from Sigma Chemical Co., St. Louis, Mo. N-acetylcysteine was obtained from Aldrich Chemical Co., Milwaukee, Wis. Captopril was kindly provided by Dr Victor Dzau. Sodium nitrite, histamine and methacholine were purchased from Fisher Scientific, Fairlawn, N.J. Leukotriene $D_4$ was purchased from Anaquest, BOC Inc., Madison, Wis. Antibiotic/antimycotic mixture (10,000 U/ml penicillin G sodium, 10,000 mcg/ml, streptomycin sulfate, 25 mcg/ml amphotericin B) was purchased from Gibco Laboratories, Grand Island, N.Y. Radioimmunoassay kits for the determination of cyclic GMP were purchased from New England Nuclear, Boston, Mass.

2. Preparation of Airways

Male Hartley guinea pigs (500–600 g) were anesthetized by inhalation of enflurane to achieve a surgical plane of anesthesia. The trachea were excised and placed in Kreb's-Henseleit buffer (mM): NaCl 118, CKl 5.4, $NaH_2PO_4$ 1.01, glucose 11.1, $NaHCO_3$ 25.0, $MgSO_4$ 0.69, CaCl 2.32, pH 7.4. The airways were then dissected free from surrounding fat and connective tissue and cut into rings 2–4 mm in diameter. The trachea rings were placed in sterile Medium 199 containing 1% antibiotic/antimycotic mixture in an atmosphere of 5% $CO_2$, 45% $O_2$, 55% $N_2$, and kept for up to 48 hours in tissue culture. The experiments were also performed on human airway smooth muscle, isolated by the same method.

3. Preparation of Blood Vessels

New Zealand White female rabbits weighing 3–4 kg were anesthetized with 30 mg/kg IV sodium pentobarbital. Descending thoracic aortic were isolated and placed immediately in a cold physiologic salt solution (Kreb's) (mM): NaCl 118, CCl 4.7, $CaCl_2$ 2.5, $MgSO_4$ 1.2, $KH_2PO_4$ 1.2, $NaHCO_3$ 12.5, and D-glucose 11.0, pH 7.4. The vessels were cleaned of adherent connective tissue, and the endothelium removed by gentle rubbing with a cotton tipped applicator inserted into the lumen, and cut into 5 mm rings.

4. Preparation of S-nitrosothiols

S-nitrosothiols were prepared at 25° C. by reacting equimolar (100 μM) concentrations of reduced thiols with $NaNO_2$ in 0.5N HCl (acidified $NaNO_2$) as described previously (Kowaluk et al., *J. Pharmacol. Exp. Ther.* 256: 1256–1264 (1990); Loscalzo et al., *J. Pharmacol. Exp. Ther.* 249(3): 726–729 (1989); and Ignarro et al., *J. Pharmacol. Exp. Ther.* 218(3): 739–749 (1981)). Solutions turned from clear to various shades of red instantaneously upon product formation, with the notable exception of S-nitroso-penicillamine, which is green.

In this method of synthesis, the reaction of thiols with NO (generated from sodium nitrite) is complete and stoichiometric (Aldred et al., *J. Chem. Soc.* Perkin Trans. II: 777–782 (1982); Byler et al., *J. Agric. Food Chem.* 31: 523–527 (1983)).

The long-carbon chain lipophilic nitrosothiols, long and short chain S-nitrosodithiols, and S-nitrosothiols with additional functional groups were synthesized by one or more of the following methods: (a) exposure to equimolar $N_2O_3$ or $N_2O_4$ in $CCl_4$, (b) exposure to equimolar acidified nitrite, (c) exposure to equimolar bubbled NO gas; (d) exposure to excess cold bubbled $NO_2$ gas; and (e) exposure to metherolic acid or equimolar $NaNO_2$ diluted in methersol.

The synthesis of S-nitroso-homocysteine has not been previously characterized. This compound displayed the distinct absorption maxima of other S-nitrosothiols at approximately 340 nm and 550 nm (Kowaluk et al., J. Pharmacol. Exp. Ther. 256: 1256–1264 (1990); Loscalzo et al., J. Pharmacol. Exp. Ther. 249(3): 726–729 (1989); and Ignarro et al., J. Pharmacol. Exp. Ther. 218(3): 739–749 (1981)). The molar absorptivity of S-nitroso-homocysteine at 547 nm is 16.7 $cm^{-1}M^{-1}$ and correlates well with published values of 16.6 and 16.1, for S-nitro-cysteine and S-nitroso-glutathione, respectively (Kowaluk et al., J. Pharmacol. Exp. Ther. 256: 1256–1264 (1990)).

Owing to the modest decay of S-nitrosothiols over time, fresh examples were made at hourly intervals and kept at 4° C. until use. Solutions were diluted as necessary into physiologic buffer immediately prior to each experiment.

5. Bioassay

Trachea and aortic rings were mounted on stirrups and connected to transducers (model FOT3C Grass) with which changes in isometric tension were measured. Rings were then suspended in 10 cc of oxygenated (95% $O_2$, 5% $CO_2$) buffer. Conditions For both the vessel and airway bioassays were established according to standard methodologies as described in Cooke et al., Am. J. Physiol. 259(3): H804–H812 (1990).

In airway experiments, the rings were equilibrated for 60 minutes under a load of 1 gm and then primed twice by exposure to 100 $\mu M$ methacholine. Tissues were contracted with various agonists at concentrations determined to generate 50% ($\pm 16\%$ S.D.) of maximum tone, after which the effects of different thiols and their S-nitrosylated derivatives were assessed. In selected experiments, relaxation responses were determined in the presence of hemoglobin, or after rings had been preexposed to methylene blue for 30 minutes.

In vessel experiments, aortic rings were contracted with 1 $\mu M$ epinephrine and relaxations were induced with S-nitrosothiols.

6. Cyclic Nucleotide Assays

The mechanism by which S-nitrosothiols relax vascular smooth muscle is felt to be through activation of guanylate cyclase with consequent increase in intracellular cyclic GMP (Ignarro et al., Circ. Res. 65: 1–21 (1989); Loscalzo et al., J. Pharmacol. Exp. Ther. 249(3): 726–729 (1989)). In order to assess this mechanism in airways, tracheal rings in Kreb's-Henseleit solution were exposed to 100 $\mu M$ S-nitroso-N-acetylcysteine (SNOAC) for 90 seconds. Reactions were terminated by the addition of ice cold 10% trichloracetic acid and rapid freezing in ethanol-saturated dry ice.

In selected experiments rings were preexposed to the guanylate cyclase inhibitor, methylene blue ($10^{-4}M$) for 30 minutes. Tissues were then individually pulverized with a glass (s) homogenizer and centrifuged at 8000 g for 5 minutes. The clear supernatant was extracted with water-saturated ether and assayed for cyclic GMP by radioimmunoassay. Acetylation of samples with acetic anhydride was used to increase the sensitivity of the assay and the determination of recoveries was aided by the use of $[^3H]$ cyclic GMP.

Dose-response relationships to SNOAC were obtained in airways contracted with 3 uM histamine, and repeated in the presence of $10^{-4}M$ hemoglobin, $10^{-5}M$ methylene blue, and $10^{-4}M$ methylene blue. Relaxation responses to SNOAC are inhibited by hemoglobin and methylene blue, with the latter in a dose-dependent manner. Cyclic GMP determinations were performed in duplicate for each experiment.

7. Statistics

All results are presented as means ± SEM. Paired samples were compared by the Student's t-test. Dose-response curves were compared by two-way analysis of variance (ANOVA). Values of $p<0.05$ were considered significant.

TABLE 1

| Inhibitory Concentrations Inducing 50% Relaxation (IC50) | |
|---|---|
| RS—NO | IC50 mean ± S.D.; × $10^{-6}$ M) |
| S-nitroso-glutathione | 0.99 ± 2.0 |
| S-nitroso-cysteine | 3.2 ± 0.2 |
| S-nitroso-homocysteine | 2.1 ± 0.3 |
| S-nitroso-N-acetylcysteine | 2.1 ± 0.8 |
| S-nitroso-penicillamine | 1.8 ± 0.8 |
| S-nitroso-captopril | 20.0 ± 0.7 |

B. Results and Discussion

The mammalian fraction of sulfur that exists as free sulfhydryl is contained largely in the form of glutathione, cysteine, and homocysteine (Jocelyn, P. C., In Biochemistry of the SH Group, Academic Press, London/New York pp. 1–46 (1972)). N-acetylcysteine is a minor metabolite of cysteine that is used for its mucolytic properties in the treatment of airway obstruction. N-acetylcysteine has also received attention within the context of nitrate metabolism and undergoes S-nitrosylation in plasma upon treatment with nitroglycerin (Fung et al., J. Pharmacol. Exp. Ther. 245(2): 524–531 (1988)). The S-nitrosylated derivatives of these four sulfhydryls comprise the group of biological S-nitrosothiols under investigation.

Captopril and penicillamine are examples of nonbiological low molecular weight thiols, and their S-nitrosylated derivatives have been well characterized (Kowaluk et al., J. Pharmacol. Exp. Ther. 256: 1256–1264 (1990); Loscalzo et al., J. Pharmacol. Exp. Ther. 249(3): 726–729 (1989); and Ignarro et al., J. Pharmacol. Exp. Ther. 218(3): 739–749 (1981).

An initial examination of the relaxant activity of each of the biological and nonbiological S-nitrosothiols in guinea pig tracheal rings was conducted. The results are shown in FIGS. 3 and 4(a)–(f). As demonstrated by dose-response relationships, these compounds are potent airway smooth muscle relaxants, with relaxant effects that are unmatched by equimolar amounts of reactant thiol or NO (generated from $NaNO_2$ alone).

In every case, the dose-response curves for the S-nitrosothiols were significantly different from the dose-response curves for NO and for the individual thiols by two-way ANOVA to $p<0.001$. Results are presented as mean ± SEM, (n=5).

With the exception of S-nitroso-captopril (SNOCAP), the S-nitrosothiols revealed comparable bioactivity with IC50s in the range of $1 \times 10^{-6}M$ (Table 1). SNOAC and SNOCAP were then selected as representative biological and nonbiological S-nitrosothiols for further detailed investigation.

Figure 5A:
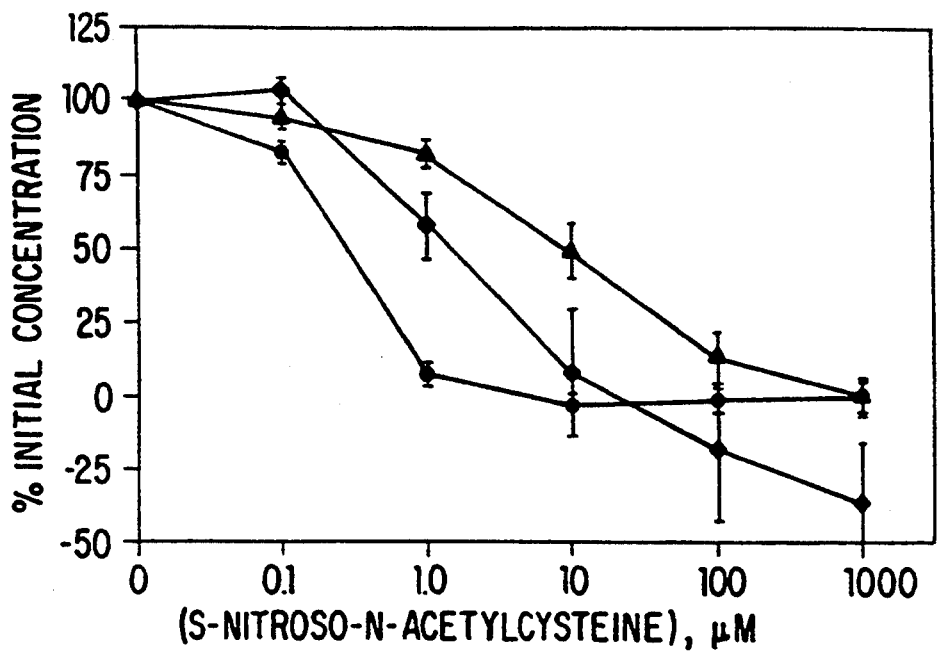
FIG. 5: Relaxant activities of S-nitroso-N-acetylcysteine (A) and S-nitroso-captopril (B) determined against contractions induced by leukotriene $D_4$, histamine and methacholine.
Figure 5B:
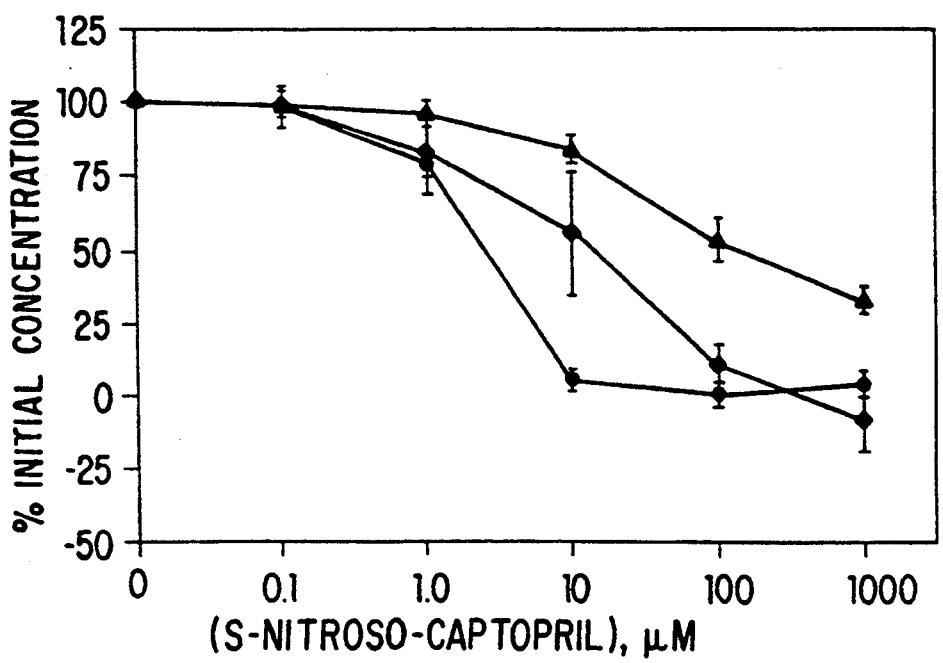

Dose-effect relationships were obtained for SNOAC and SNOCAP using tracheal rings induced to constrict with leukotriene D4, histamine, and methacholine. As shown in FIG. 5, airways exhibited agonist specificity toward S-nitrosothiol-mediated relaxations: S-nitrosothiols were most active for relaxation of leukotriene D4-induced contractions and progressively less effective with contractions induced by histamine and methacholine. In every case, SNOAC was approximately 10-fold more active in relaxation of airways than SNO-CAP. Results are presented as mean ± SEM (n=3–5).

Figure 6:
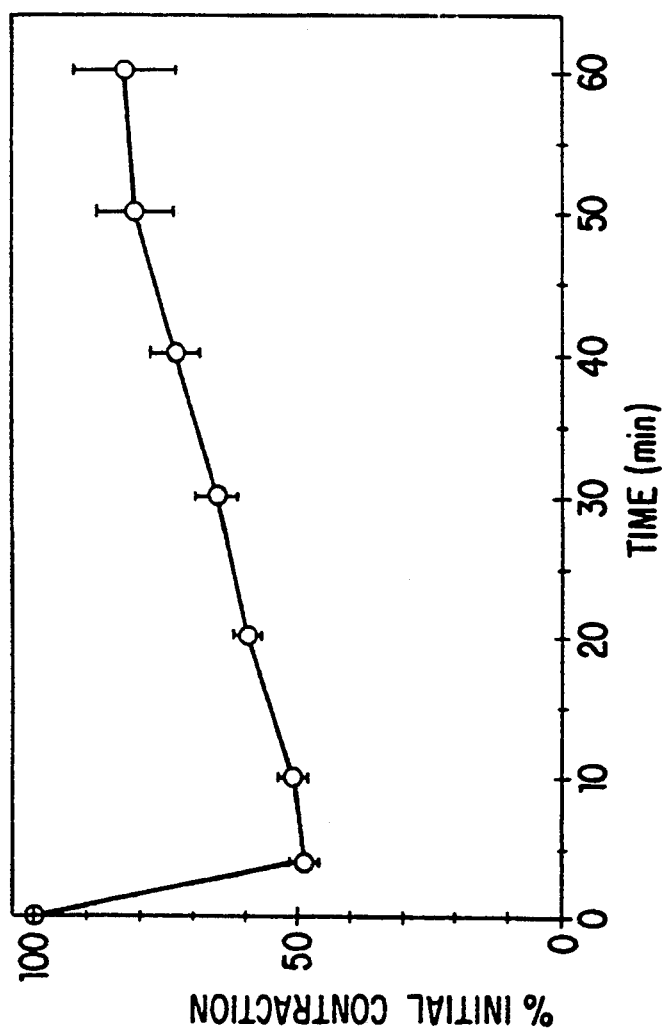
FIG. 6: The course of relaxation induced by S-nitroso-N-acetylcysteine ($5 \times 10^{-6}$M) over 60 minutes.

The time course of relaxation to SNOAC is shown in FIG. 6. Using a concentration ($5 \times 10^{-6}$M) selected to induce approximately 50% of the maximal response, maximal relaxation occurred by five minutes and a significant residual loss of tone was still evident at one hour. In control experiments, airway contractions remained stable over the study period.

These relaxation responses contrast markedly with those generally ascribed to low-molecular-weight S-nitrosothiols. FIG. 7 illustrates the notable difference in relaxation kinetics between these tissues. In vascular smooth muscle, the relaxations are rapid and transient, whereas in tracheal smooth muscle, relaxations occur more slowly and persist for a much longer duration.

Figure 8:
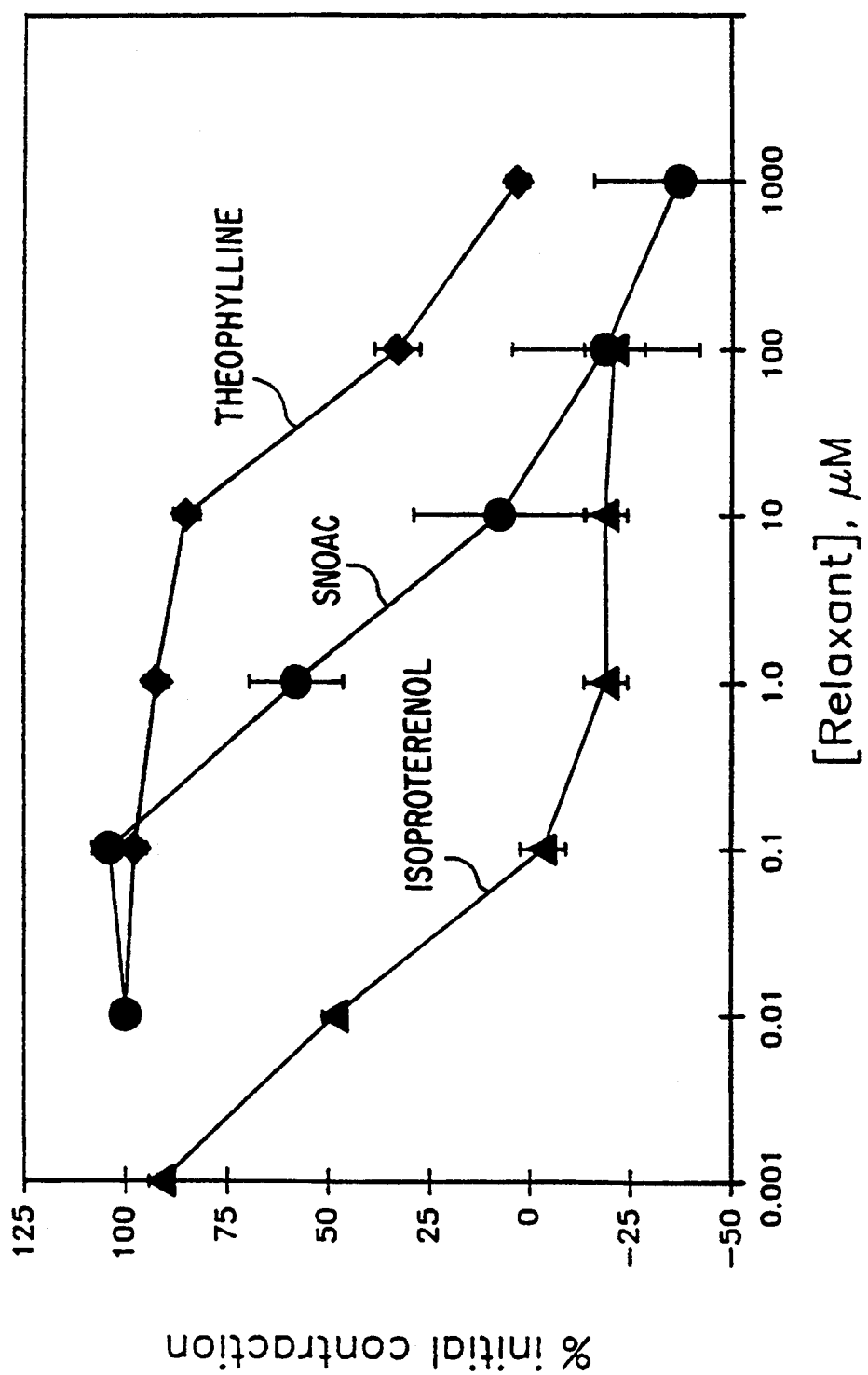
FIG. 8: Tracheal relaxant effects of S-nitroso-N-acetylcysteine, isoproterenol, and theophylline.

FIG. 8 shows a comparison between the efficacy of SNOAC and isoproterenol or theophylline under identical study conditions. Of the drugs evaluated, isoproterenol was the most active relaxant, however, SNOAC was approximately 50 times more active in relaxation than theophylline. The dose response curves for these agents are each significantly different from each other by two-way ANOVA to $p<0.01$. Results are expressed as mean ± SEM (n=3–5).

Figure 9:
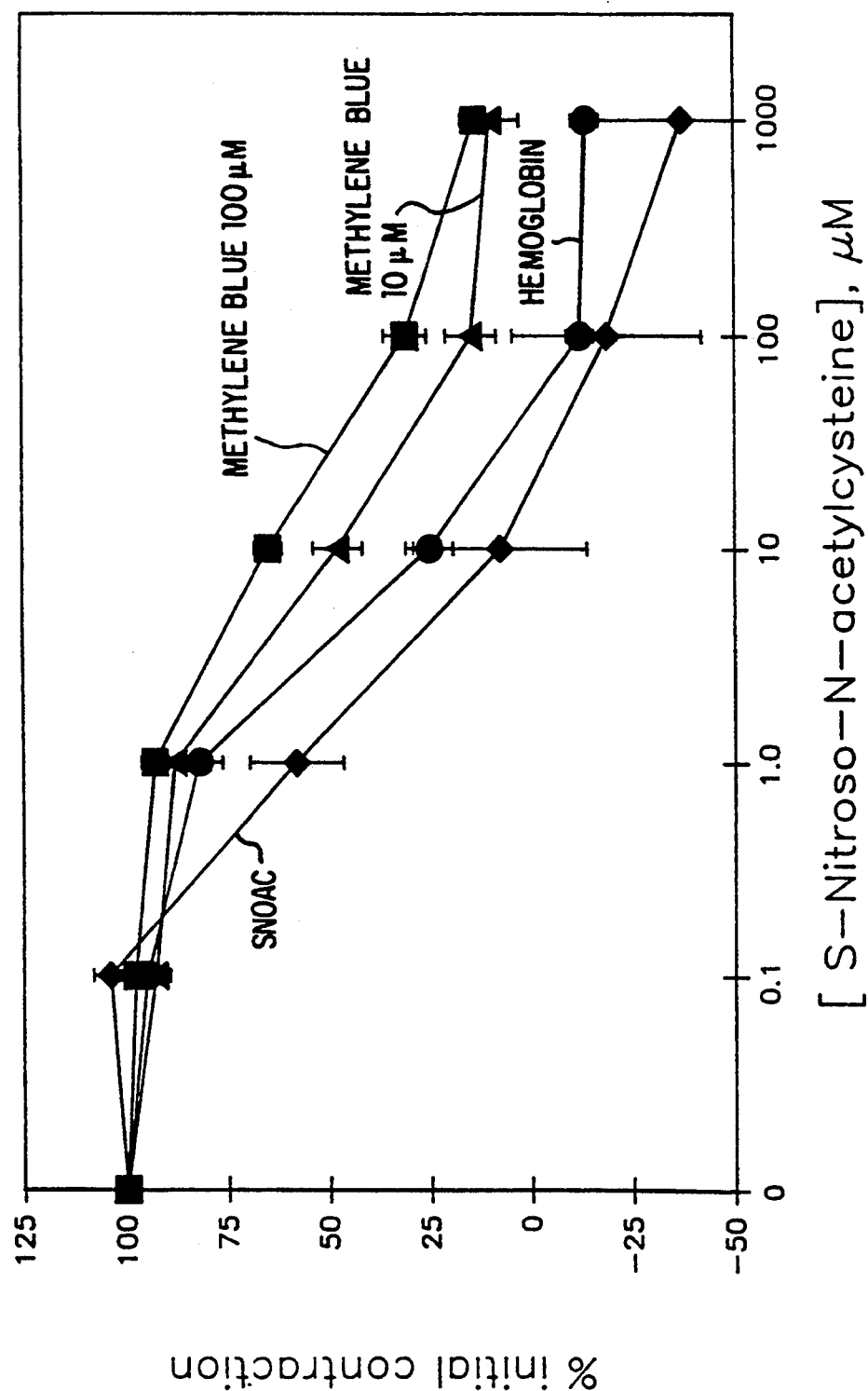
FIG. 9: Inhibition of tracheal relaxation to S-nitroso-N-acetylcysteine by hemoglobin and methylene blue.

Hemoglobin and methylene blue are established inhibitors of NO-induced relaxations in vascular smooth muscle (Ignarro et al., *Circ. Res.* 65: 1–21 (1989)). When their effects were examined in guinea pig airways, hemoglobin and methylene blue each partially attenuated (only 10–20% attenuation) the actions of SNOAC, as evidenced by rightward shifts in the dose-effect relationships to SNOAC in their presence (FIG. 9). In human airways, neither hemoglobin or methylene blue attenuated the relaxation effect. The dose-response curves for SNOAC were significantly different from each of the curves derived in the presence of hemoglobin and methylene blue by two-way ANOVA to $p=0.05$. Results are presented as mean ± SEM (n=3–5).

Figure 10:
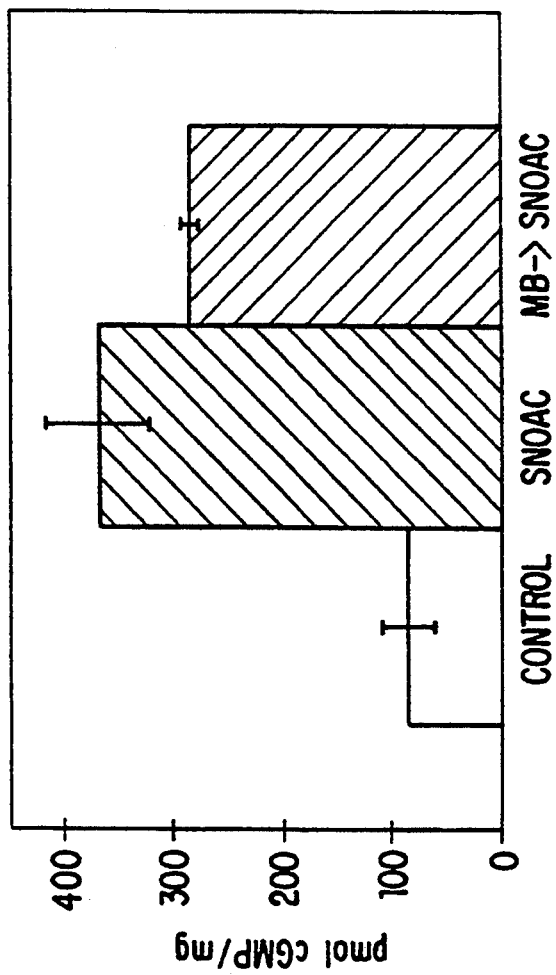
FIG. 10: Cyclic GMP determinations in tracheal rings incubated with 100 µM S-nitroso-N-acetylcysteine.

The biochemical mechanism of action of S-nitrosothiols was further investigated in isolated tracheal rings. As shown in FIG. 10, tracheal rings incubated with SNOAC exhibited 4-fold increases in cyclic GMP over basal levels (control). Increases in cyclic GMP were attenuated by pretreatment of tissues with the guanylate cyclase inhibitor, methylene blue ($10^{-4}$M). Cyclic GMP levels in the presence of SNOAC were significantly greater than control values ($p<0.0005$) and levels determined in the presence of methylene blue ($p=0.05$). Results are presented as mean ± SEM (n=4–8).

Figure 11:
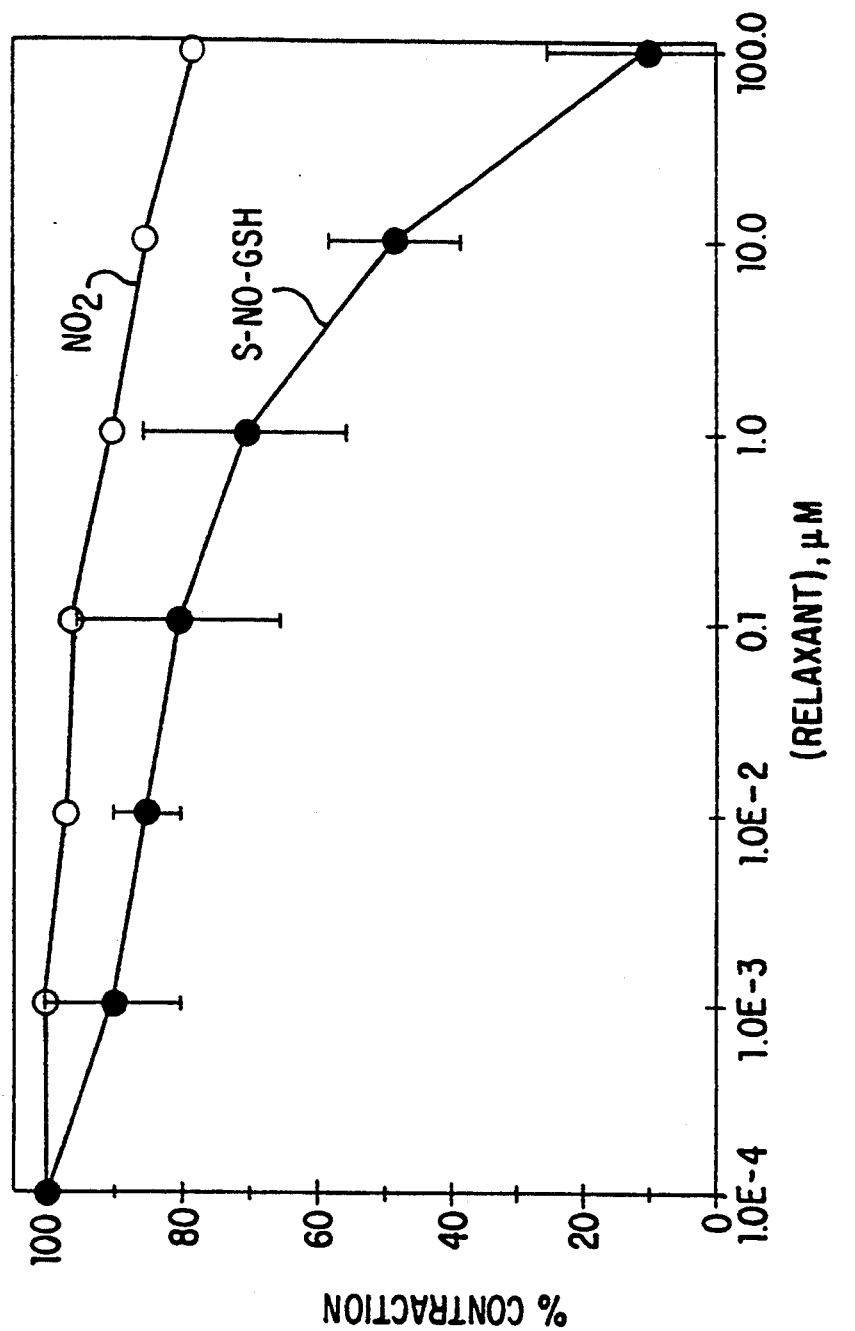
FIG. 11: Comparison between the relaxant effect of S-nitroso-glutathione and nitrite upon human tracheal smooth muscle.
Figure 12:
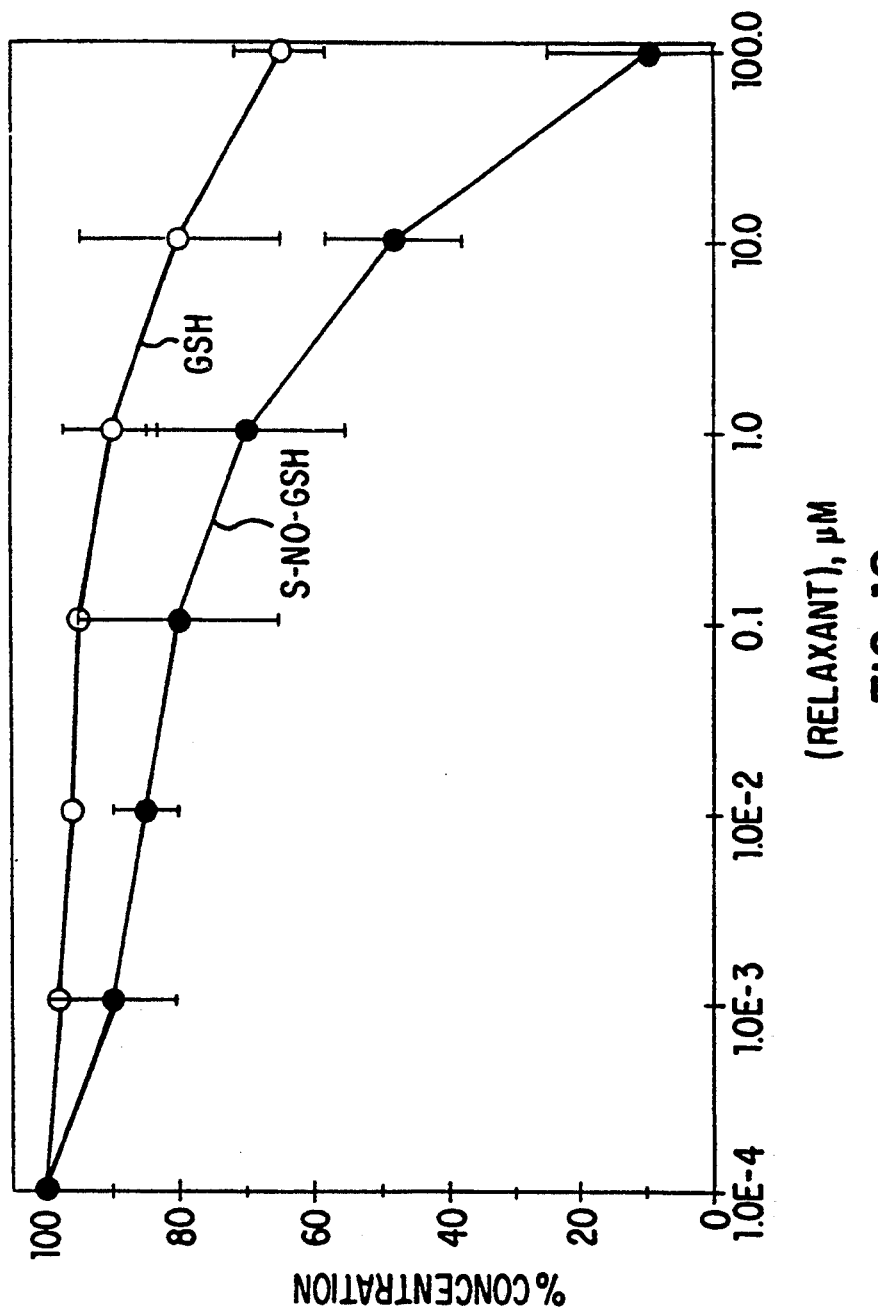
FIG. 12: Comparison between the relaxant effect of S-nitroso-glutathione and glutathione upon human tracheal smooth muscle.

An examination of the relaxant activity of S-nitrosothiols in human tracheal rings was also conducted. The results are shown in FIGS. 11–15. In particular, FIG. 11 shows that S-nitroso-glutathione has a relaxant effect upon human trachea which is significantly greater than nitrite ($NO_2$). FIG. 12 demonstrates that the relaxant effect of S-nitroso-glutathione upon human trachea is significantly greater than glutathione alone. This data underscores the fact that the bioactivity of nitric oxide in airways depends upon the form in which it is delivered. S-nitrosothiols provide efficient delivery of NO in its most bioactive and non-toxic form.

Figure 13:
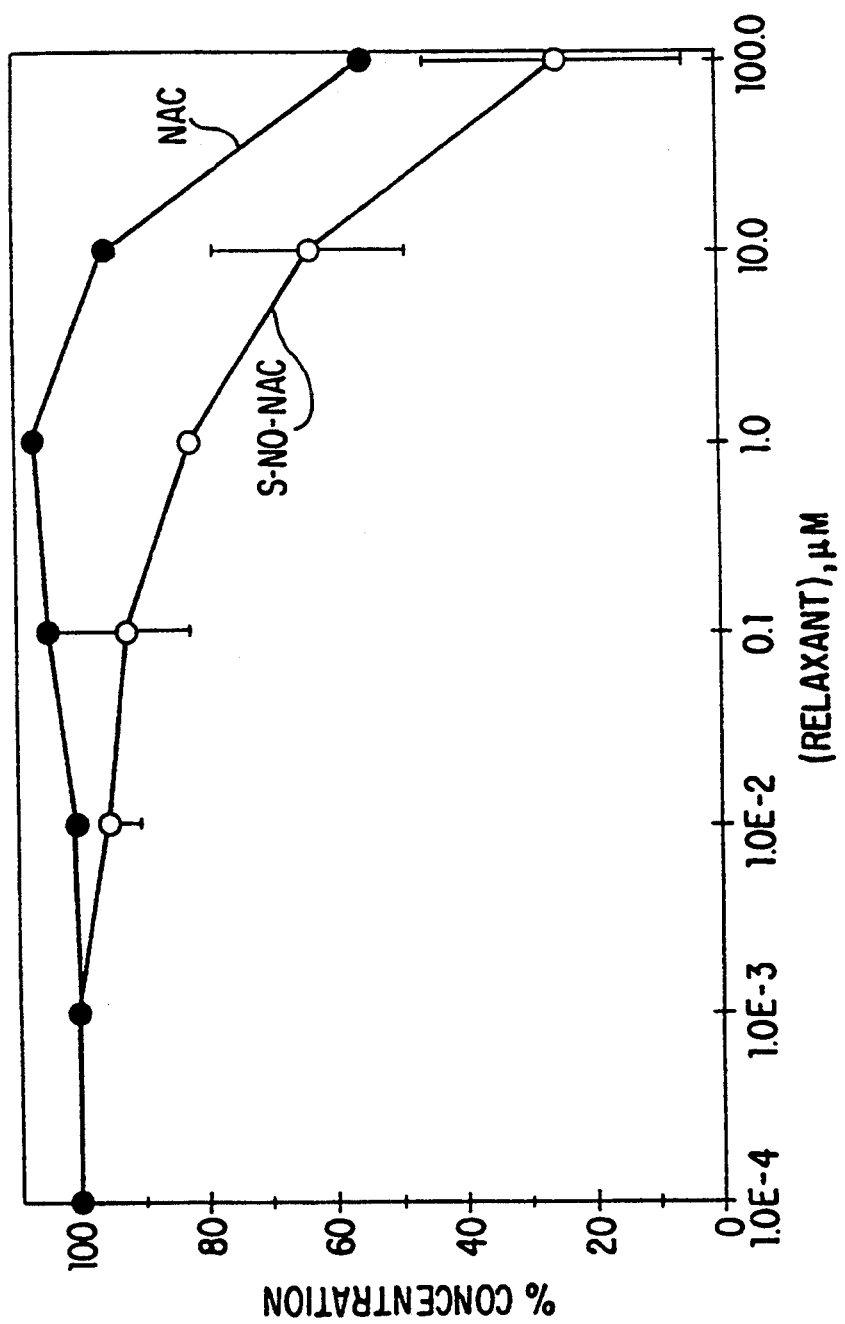
FIG. 13: Comparison between the relaxant effect of S-nitroso-N-acetylcysteine and N-acetylcysteine upon human tracheal smooth muscle.

FIG. 13 demonstrates that the relaxant effect of SNOAC upon human trachea is significantly greater than that of N-acetylcysteine. As shown in FIG. 13, NAC caused significant constriction of the tracheal smooth muscle, which is consistent with the fact that NAC, when given as a mucolytic agent, causes the untoward side effect of bronchospasm. SNOAC not only causes relaxation of airway tissue, but also eliminates bronchospasm.

Figure 14:
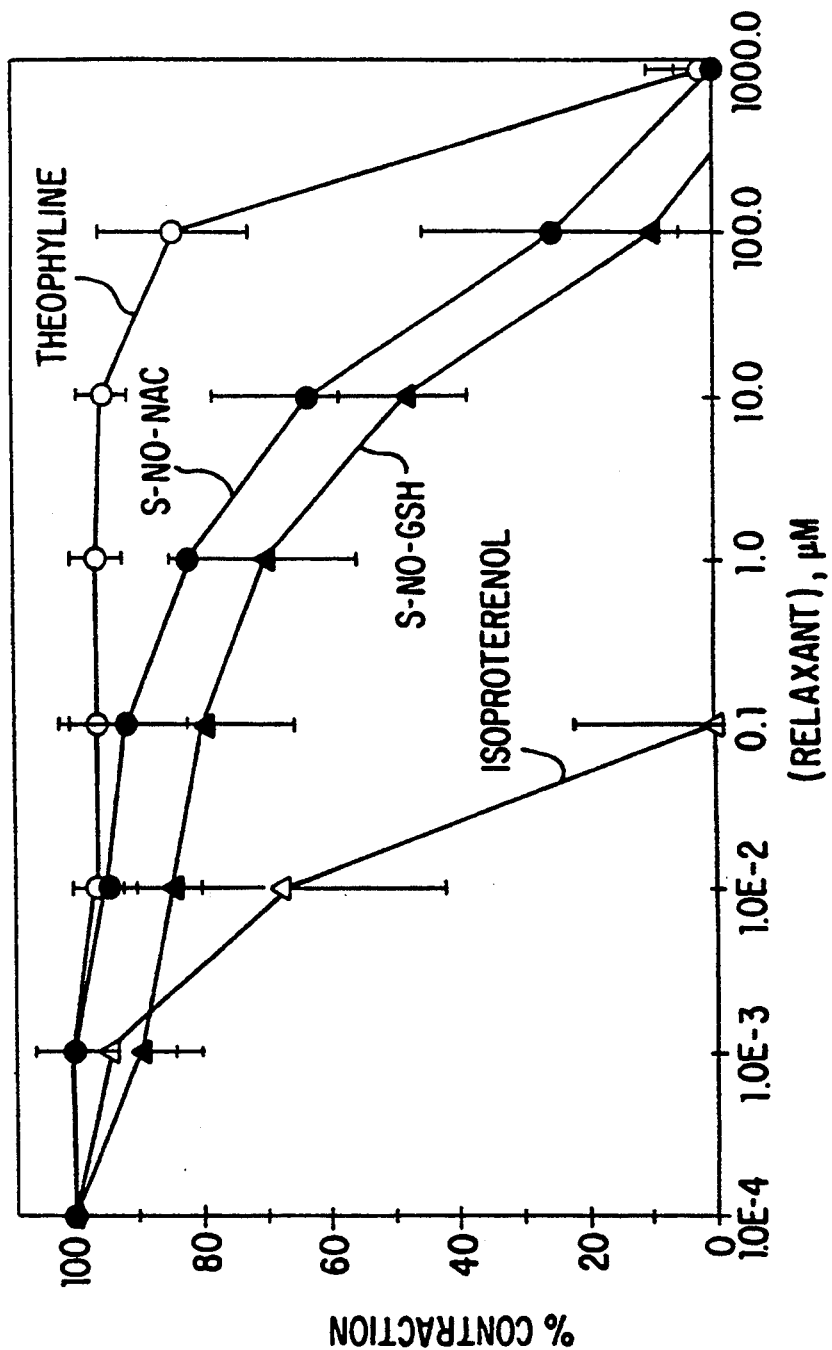
FIG. 14: Tracheal relaxant effects of theophylline, isoproterenol, S-nitroso-N-acetylcysteine, and S-nitroso-glutathione.

FIG. 14 demonstrates that SNOAC and SNOGSH exert a relaxant effect on airway smooth muscle which is significantly more potent than that of theophylline, and compares favorably with that exerted by isoproterenol.

Figure 15:
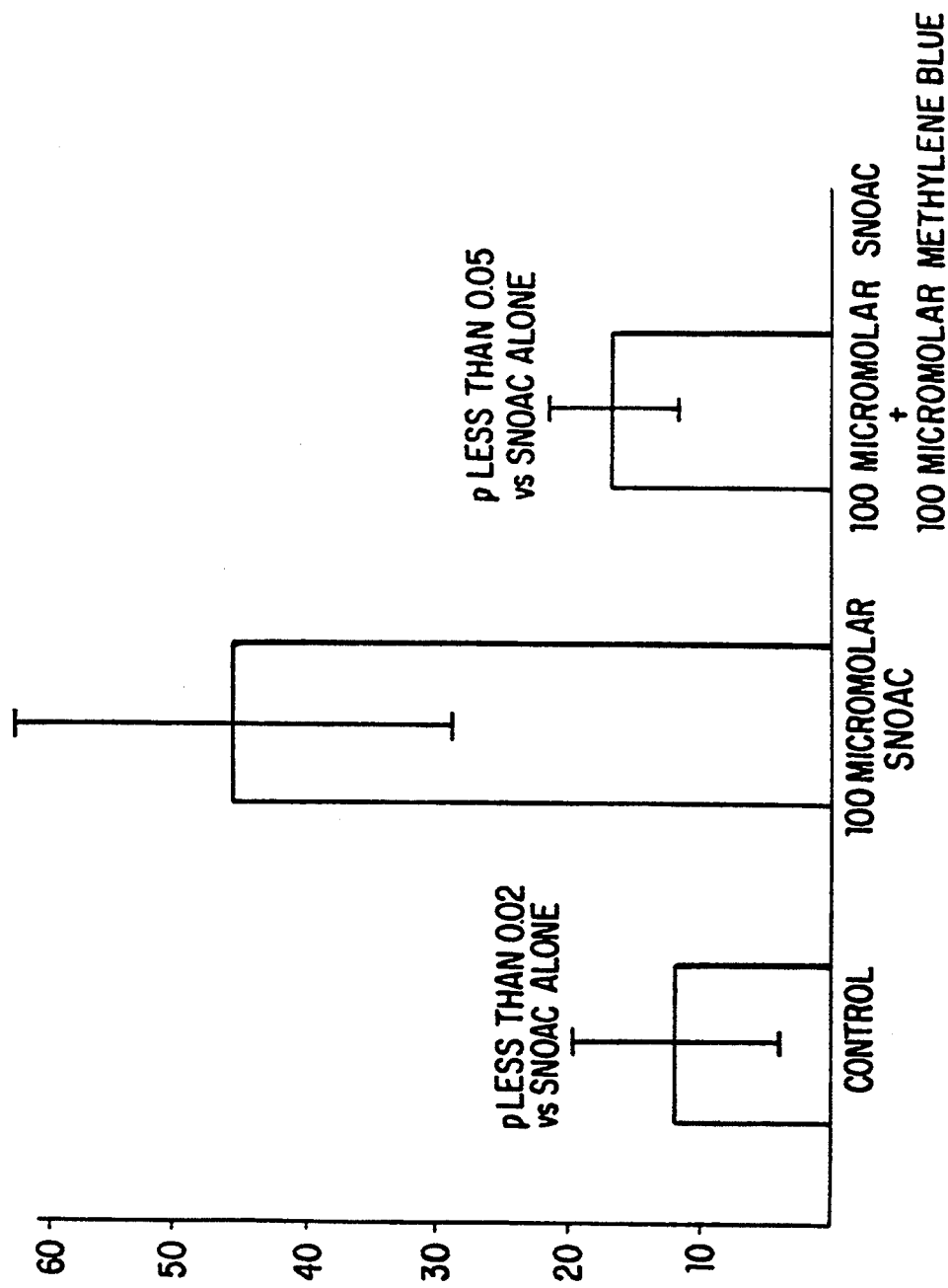
FIG. 15: Cyclic GMP response to S-nitroso-N-acetylcysteine in human airways.

Experiments were also conducted to assess the cGMP response to SNOAC in human airways. As shown in FIG. 15, tracheal rings incubated with SNOAC exhibited 4-fold increases in cyclic GMP over basal levels (control).

Unexpectedly, the relaxation response to low molecular weight S-nitrosothiols in airways differs markedly from that observed in blood vessels. In the latter case, relaxations occur slowly and persist for a much longer duration. This is most likely attributed to the inherent differences between vascular and nonvascular smooth muscle. There may be additional contributing factors responsible for this heterogeneity. Finally, any disparity among smooth muscle cells in redox state, availability of reducing equivalents, pH, oxygen tension, or any other factor that might influence the stability of the S—NO bond would be predicted to influence relaxation kinetics.

The results also suggests that, in addition to the primary site of obstruction in the lung, the efficacy of nitro(so)-bronchodilators may be determined by the nature of the chemical mediators contributing to bronchoconstriction. In particular, S-nitrosothiols were most effective in this study against leukotriene D4-mediated bronchoconstriction and progressively less effective against histamine and methacholine-mediated constriction. Thus, regional variation in guanylate cyclase content or activity, the site of obstruction, the form in which the active species of NO is administered, and the nature of the bronchoconstrictor stimuli are all variables which may influence the determination of nitro(so)-bronchodilator efficacy and the importance of guanylate cyclase in regulating airway tone.

Example 2

Guanylate Cyclase Inhibitors Do Not Inhibit S-nitrosothiol Induced Relaxation in Human Airways The effect of guanylate cyclase inhibitors upon S-nitrosothiol-induced airway relaxation and cGMP increase was assessed, using the previously described bioassay and cyclic nucleotide assay procedures. Bronchodilator effects of S-NOGSH and SNOAC were examined in human airways (5–12 mm outer diameter). Concentration-response relationships for rings contracted with methacholine (7 μM) resulted in IC50 values of 22 μM, approximately two orders of magnitude greater than theophylline.

Figure 16:
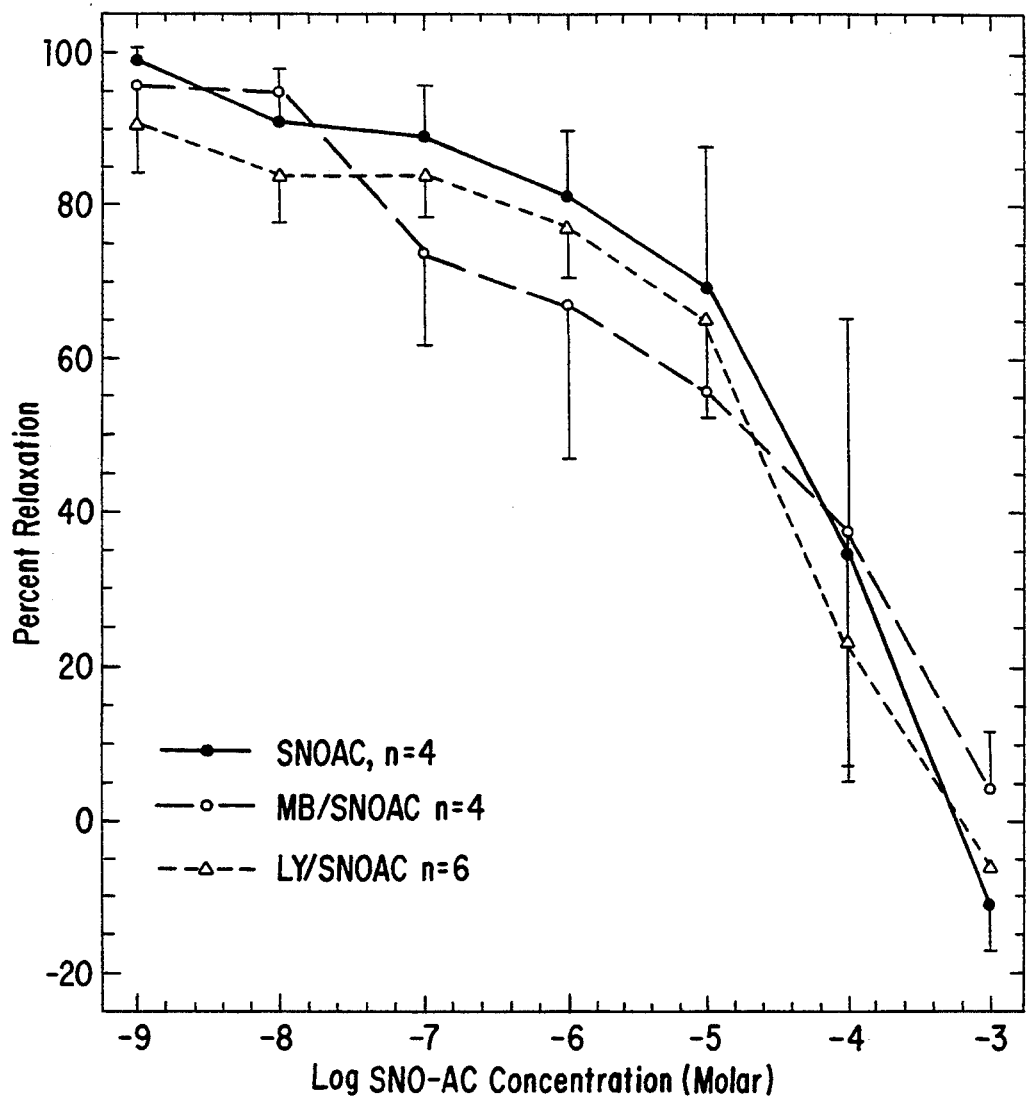
FIG. 16: SNOAC-induced airway relaxation is not inhibited by methylene blue.

SNOAC (100 mm) induced 4-fold increases ($P<0.02$), over control airway cGMP levels, as shown in Table 3. However, as shown in FIG. 16, SNOAC-induced airway relaxation was not significantly inhibited by methylene blue ($10^{-4}$) or LY83583 ($5 \times 10^{-5}$). Similarly, hemoglobin (100 µM) had little effect on S-nitrosothiol-induced relaxation (P=NS).

These results demonstrate that the mechanism by which S-nitrosothiols cause airway relaxation is not due solely to increases in cGMP. Thus, S-nitrosothiols cause airway relaxation through both increase in cyclic GMP, as well as a cGMP-independent pathway.

Example 3

S-nitrosothiols Resist Decomposition In the Presence of Redox Metals

The stability of SNOAC and SNOGSH in the presence of oxygen and redox metals was assessed. When subjected to conditions consisting of 95% $O_2$, pH 7.4, the half lives of these compounds were shown to be on the order of hours, and significantly greater than that of NO, or NO., which, under similar conditions, are on the order of seconds.

In addition, S-nitrosothiol stability was assessed in the presence of various redox metals or chelating agents. These compounds were resistant to decomposition when $Cu^+$, $Fe^{2+}$, or $Cu^{2+}$ (50 µM) or defuroxamine or EDTA (10 µM) were added. Thus, these experiments demonstrate that, unlike NO., S-nitrosothiols are not rapidly inactivated in the presence of oxygen, nor do they decompose in the presence of redox metals.

Example 4

S-nitrosothiols Increase Hemoglobin-oxygen Binding

Figure 17:
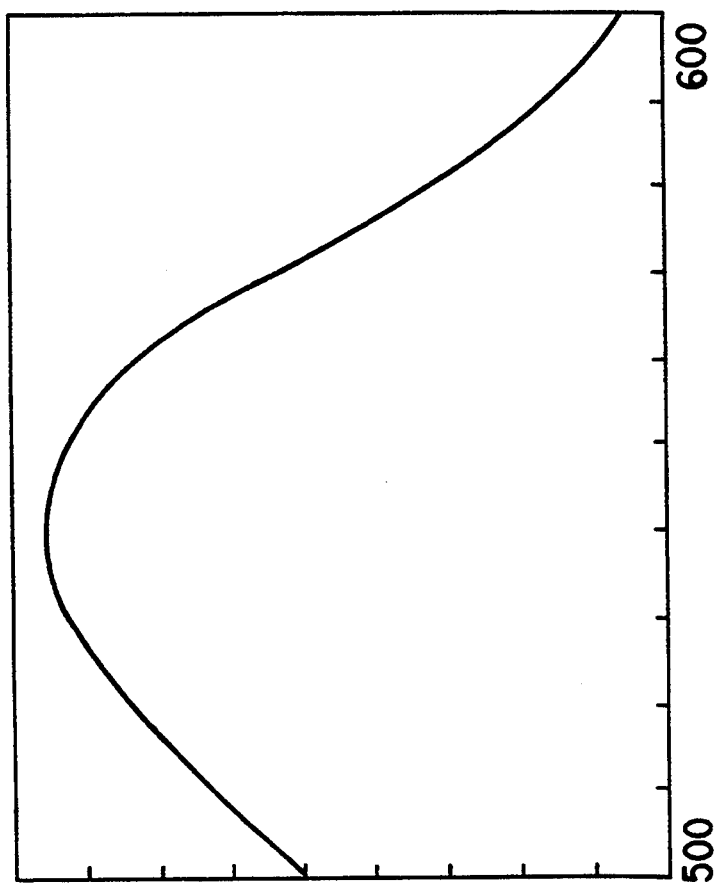
FIG. 17: S-nitrosylation of hemoglobin.

Additional experiments were conducted to evaluate the reaction between S-nitrosothiols and hemoglobin. S-nitrosylation of hemoglobin was accomplished by reacting 12.5 µMol hemoglobin with 12.5 µM SNOAC for 5 and 20 minute intervals (pH 6.9). S-nitrosylation was verified, using standard methods for detection of S-nitrosothiols (Saville, Analyst 83: 670–672 (1958)). The Saville method, which assays free $NO_x$ in solution, involves a diazotization reaction with sulfanilamide and subsequent coupling with the chromophore N-(1-naphthyl)ethylenediamine. The specificity for S-nitrosothiols derives from assay determinations performed in the presence and absence of $HgCl_2$, the latter reagent catalyzing the hydrolysis of the S—NO bond. Confirmatory evidence for S-nitrosothiol bond formation was obtained by spectrophotometry, demonstrated by the absorption maximum of 450 nm, as shown in FIG. 17. This was demonstrated using $NO^+$ equivalents in the form of SNOAC.

Figure 18:
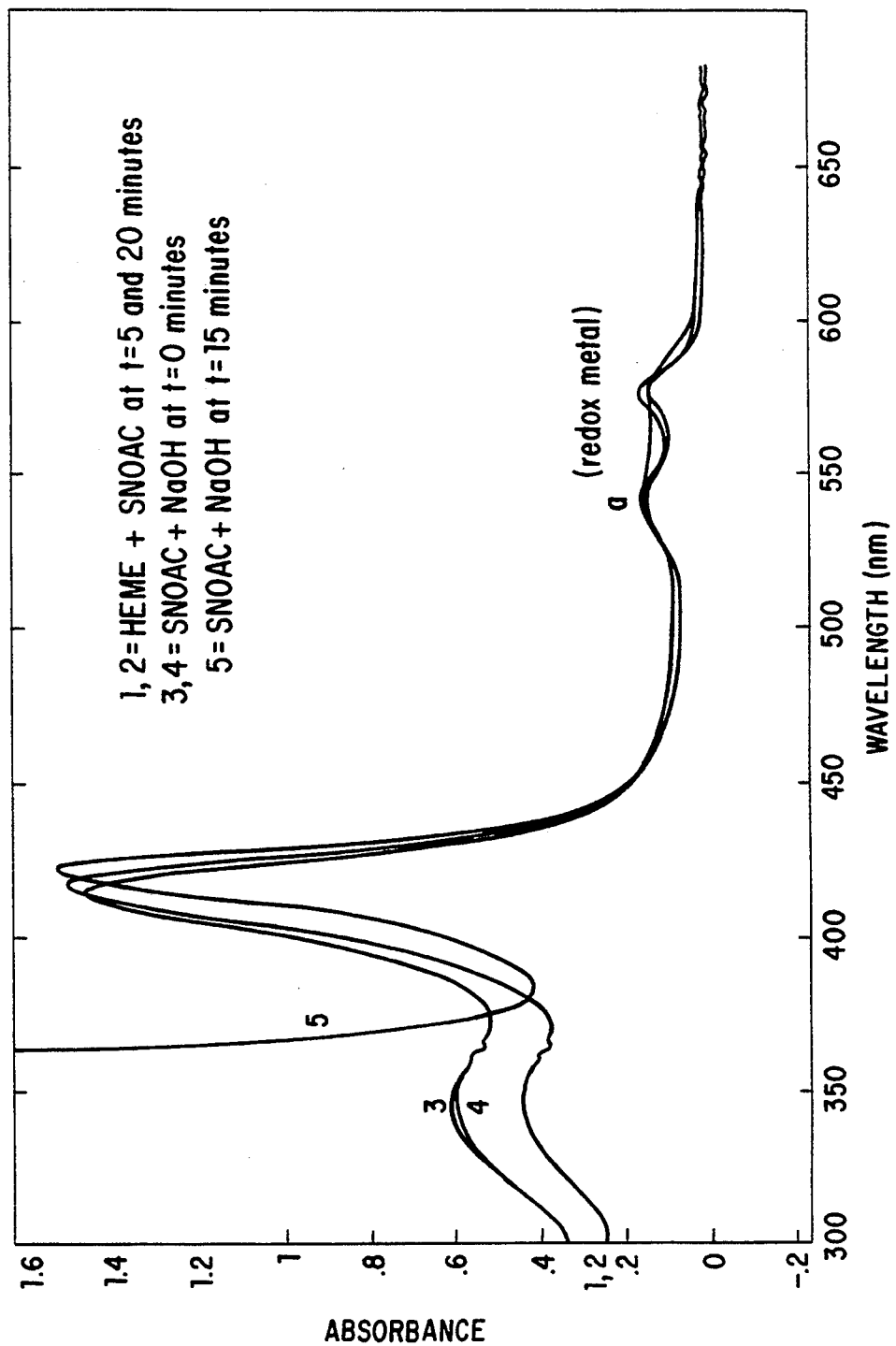
FIG. 18: UV spectrum of hemoglobin incubated with S-nitroso-N-acetylcysteine.
Figure 19:
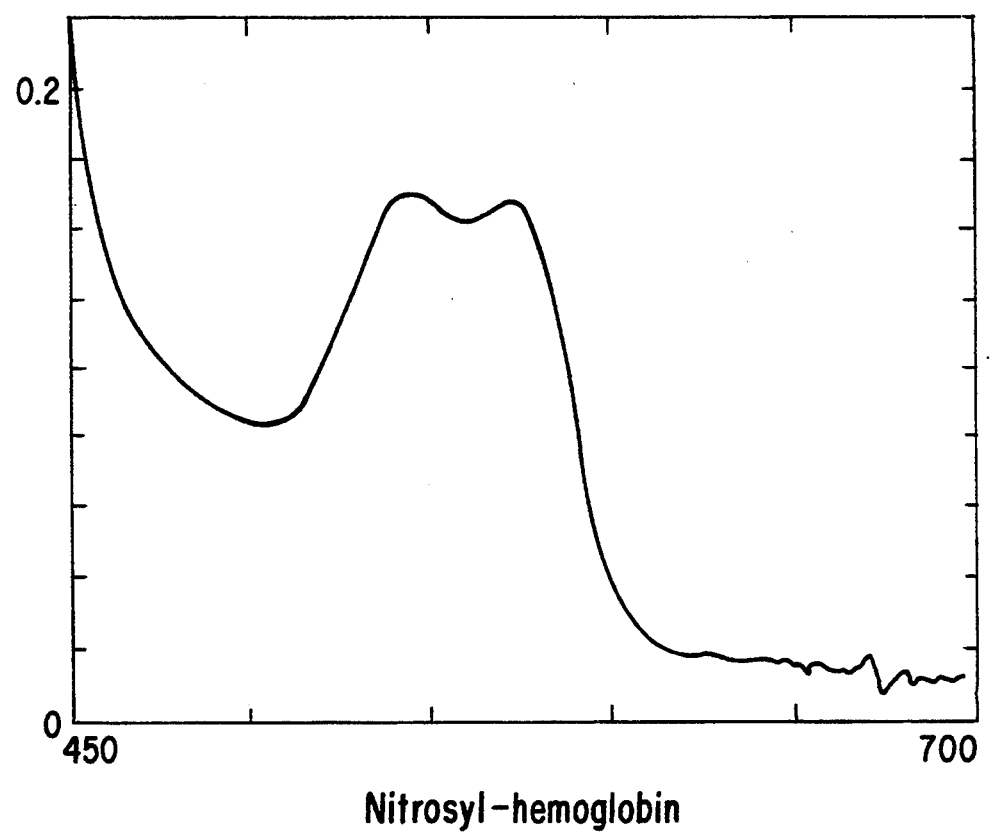
FIG. 19: Reaction of nitric oxide at the iron-binding site of hemoglobin.

As demonstrated by FIG. 18, the UV spectrum of hemoglobin incubated with SNOAC shows no reaction at the redox metal (iron-binding site) of hemoglobin, over 15 minutes. For the purposes of comparison, equimolar concentrations of hemoglobin and $NaNO_2$ were reacted in 0.5N HCl, to form nitrosyl-hemoglobin, and the UV spectrum was obtained. As shown in FIG. 19, NO reacted instantaneously with the redox metal site on hemoglobin. The fact that the S-nitrosothiol did not react with the redox metal site of hemoglobin, but with its thiol group instead, indicates that the reactive NO species donated by the S-nitrosothiol is nitrosonium or nitroxyl.

S-nitrosylation of hemoglobin does not result in the formation of methemoglobin and consequent impairment in hemoglobin-oxygen binding. Furthermore, an additional experiment demonstrated that S-nitrosylation of hemoglobin causes a leftward shift in the hemoglobin-oxygen association curve, indicating an increase in oxygen binding. Thus, the reaction between S-nitrosothiols and hemoglobin not only eliminates the inhibition of oxygen binding which occurs from the reaction with NO., but actually increases binding and oxygenation of the blood.

In summary, S-nitrosothiols are important intermediates in the metabolism of organic nitrates and endogenously-derived NO. Furthermore, these compounds provide greater stability, a longer half life than NO, and retain its cyclic GMP-dependent bioactivity in blood vessels.

In the present invention, the inventors have demonstrated that S-nitrosothiols are also potent airway smooth muscle relaxants and mediate their effects through both activation of guanylate cyclase, and a cGMP-independent mechanism. The results indicate that there are a number of important mediators of airway tone, including cGMP. The results also demonstrate a mechanism by which the bioactivity of NO is preserved in the presence of high ambient concentrations of oxygen and reactive oxygen species and redox metals.

In addition to the relaxant effect exerted upon airways, S-nitrosothiols also increase hemoglobin-oxygen binding, thus providing a means for enhancing oxygenation of the blood and oxygen transport to tissues. As a result of the potent effects exerted by S-nitrosothiols on airway relaxation and blood oxygenation, these compounds have significant pharmacological utility for the treatment of airway obstruction, or other disorders resulting in insufficient blood oxygenation.

TABLE 3

| cGMP LEVELS IN HUMAN AIRWAYS | |
|---|---|
| | cGMP (Pmol/gm) |
| Control | 12 ± 8 |
| SNOAC | 46 ± 17* |
| SNOACC + M.B. | 17 ± 5 | p < 0.05 c/w control and MB (methylene blue)

What is claimed is:

1. A method for relaxing airway smooth muscle in an individual in need thereof, comprising administering an airway smooth muscle relaxing amount of a compound selected from the group consisting of S-nitroso-N-acetylcysteine, S-nitroso-glutathione and S-nitroso-homocysteine to a human in need thereof.

2. The method of claim 1 wherein said compound is administered in a pharmaceutical composition which includes a pharmaceutically acceptable carrier.

3. The method of claim 2 wherein said pharmaceutical composition is administered by a route comprising oral, sublingual, intravenous, intramuscular, aerosol, topical or bronchoscopic delivery.

4. A method for treatment or prevention of respiratory disorders involving airway smooth muscle contraction, comprising administering an amount effective to treat or prevent respiratory disorders involving airway smooth muscle contraction of a compound selected from the group consisting of S-nitroso-N-acetylcysteine, S-nitroso-glutathione and S-nitroso-homocysteine to a human in need thereof.

5. The method of claim 4 wherein said compound is administered in a pharmaceutical composition which includes a pharmaceutically acceptable carrier.

6. The method of claim 5 wherein said pharmaceutical composition is administered by a route comprising oral, sublingual, intravenous, intramuscular, aerosol topical or bronchoscopic delivery.

7. The method of claim 4 wherein said respiratory disorder is obstructive lung disease selected from the group consisting of emphysema, asthma bronchitis, fibrosis, excessive mucous secretion, obstruction of air flow, and lung disorders resulting from post-surgical complications.

8. A method for relaxing gastrointestinal smooth muscle, comprising administering a gastrointestinal smooth muscle relaxing amount of a compound selected from the group consisting of S-nitroso-N-acetylcysteine, S-nitroso-glutathione, and S-nitroso-homocysteine to a human in need thereof.

9. The method of claim 8 wherein said compound is administered in a pharmaceutical composition which includes a pharmaceutically acceptable carrier.

10. The method of claim 9 wherein said pharmaceutical composition is administered by a route comprising oral, sublingual, intravenous, topical, intramuscular, aerosol or endoscopic delivery.

11. A method for alleviating contraction or spasm of gastrointestinal smooth muscle associated with endoscopic procedures comprising, administering an amount effective for alleviating contraction or spasm of gastrointestinal smooth muscle associated with endoscopic procedures of a compound selected from the group consisting of S-nitroso-N-acetylcysteine, S-nitroso-glutathione and S-nitroso-homocysteine to a human in need thereof.

12. The method of claim 11 wherein said compound is administered in a pharmaceutical composition which includes a pharmaceutically acceptable carrier.

13. The method of claim 12 wherein said pharmaceutical composition is administered by a route comprising oral, sublingual, intravenous, topical, intramuscular, aerosol or endoscopic delivery.

14. A method for relaxing corpus cavernosum smooth muscle, comprising, administering a corpus cavernosum smooth muscle relaxing amount of a compound selected from the group consisting of S-nitroso-N-acetylcysteine, S-nitroso-glutathione and S-nitroso-homocysteine to a human in need thereof.

15. The method of claim 14 wherein said compound is administered in a pharmaceutical composition which includes a pharmaceutically acceptable carrier.

16. The method of claim 15 wherein said pharmaceutical composition is administered by a route comprising oral, sublingual, intravenous, topical, intramuscular or aerosol delivery.

17. A method for relaxing bladder smooth muscle, comprising administering a bladder smooth muscle relaxing amount of a compound selected from the group consisting of S-nitroso-N-acetylcysteine, S-nitroso-glutathione and S-nitroso-homocysteine to a human in need thereof.

18. The method of claim 17 wherein said compound is administered in a pharmaceutical composition which includes a pharmaceutically acceptable carrier.

19. The method of claim 18 wherein said pharmaceutical composition is administered by a route comprising oral, sublingual, intravenous, topical, intramuscular or aerosol delivery.

20. A method for relaxing uterine smooth muscle, comprising administering a uterine smooth muscle relaxing amount of a compound selected from the group consisting of S-nitroso-N-acetylcysteine, S-nitroso-glutathione and S-nitroso-homocysteine to a human in need thereof.

21. The method of claim 20 wherein said compound is administered in a pharmaceutical composition which includes a pharmaceutically acceptable carrier.

22. The method of claim 21 wherein said pharmaceutical composition is administered by a route comprising oral, sublingual, intravenous, topical, intramuscular or aerosol delivery.

23. A method for relaxing non-vascular smooth muscle, comprising:
administering a non-vascular smooth muscle relaxing amount of a compound selected from the group consisting of S-nitroso-N-acetylcysteine, S-nitroso-glutathione and S-nitroso-homocysteine to a human in need thereof.

* * * * *